(12) United States Patent
Komatsu et al.

(10) Patent No.: US 10,543,132 B2
(45) Date of Patent: *Jan. 28, 2020

(54) ABSORBENT ARTICLE WITH BLOOD MODIFYING AGENT

(75) Inventors: Shimpei Komatsu, Kanonji (JP); Yuki Noda, Kanonji (JP); Mitsuhiro Wada, Kanonji (JP); Akira Hashino, Kanonji (JP); Hideyuki Kinoshita, Kanonji (JP); Masashi Nakashita, Kanonji (JP); Ichiro Wada, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 867 days.

This patent is subject to a terminal disclaimer.

(21) Appl. No.: 14/008,810

(22) PCT Filed: Mar. 23, 2012

(86) PCT No.: PCT/JP2012/058499
§ 371 (c)(1),
(2), (4) Date: Aug. 22, 2014

(87) PCT Pub. No.: WO2012/133724
PCT Pub. Date: Oct. 4, 2012

(65) Prior Publication Data
US 2014/0358102 A1    Dec. 4, 2014

(30) Foreign Application Priority Data

Mar. 31, 2011 (JP) ................................. 2011-079446
Sep. 2, 2011 (JP) ................................. 2011-192144

(51) Int. Cl.
A61F 13/511 (2006.01)
A61L 15/20 (2006.01)
A61L 15/44 (2006.01)

(52) U.S. Cl.
CPC ......... *A61F 13/51113* (2013.01); *A61L 15/20* (2013.01); *A61L 15/44* (2013.01); *A61L 2300/216* (2013.01)

(58) Field of Classification Search
CPC .......... A61F 13/47263; A61F 13/51108; A61F 13/5113; A61F 13/8405; A61F 2013/8455;
(Continued)

(56) References Cited

U.S. PATENT DOCUMENTS 3,929,135 A    12/1975   Thompson
4,588,630 A     5/1986   Shimalla
(Continued)

FOREIGN PATENT DOCUMENTS

CN    1432352 A      7/2003
EP    1250940 A1    10/2002
(Continued)

OTHER PUBLICATIONS

MSDS for Arlamol PC-10 print date Apr. 22, 2016.*
(Continued)

*Primary Examiner* — Kathryn E Ditmer
(74) *Attorney, Agent, or Firm* — Hauptman Ham, LLP

(57) ABSTRACT

An absorbent article includes a liquid-permeable top sheet, a liquid-impermeable back sheet, and an absorbent body between the liquid-permeable top sheet and liquid-impermeable back sheet. The liquid-permeable top sheet includes a blood modifying agent with an IOB of 0.00-0.60, a melting point of no higher than 45° C., a water solubility of 0.00-0.05 g in 100 g of water at 25° C., and a weight-average molecular weight of no greater than 1,000.

10 Claims, 3 Drawing Sheets

(58) Field of Classification Search
CPC .......... A61L 15/20; A61L 15/34; A61L 15/42;
A61L 15/48; A61L 15/50
See application file for complete search history.

(56) References Cited

U.S. PATENT DOCUMENTS

| | | | |
|---|---|---|---|
| 4,759,754 A | 7/1988 | Korpman | |
| 5,078,710 A | 1/1992 | Suda et al. | |
| 5,334,176 A | 8/1994 | Buenger et al. | |
| 5,344,416 A | 9/1994 | Niihara | |
| 5,614,283 A | 3/1997 | Potnis et al. | |
| 5,650,214 A | 3/1997 | Anderson et al. | |
| 6,153,209 A | 11/2000 | Vega et al. | |
| 6,548,732 B2 * | 4/2003 | Erdman | A61F 13/475 424/402 |
| 6,730,819 B1 | 5/2004 | Pesce | |
| 2001/0029141 A1 | 10/2001 | Mizutani et al. | |
| 2003/0088222 A1 | 5/2003 | Yoshimasa et al. | |
| 2003/0149410 A1 | 8/2003 | Kudo et al. | |
| 2003/0198784 A1 | 10/2003 | Mizutani et al. | |
| 2004/0024374 A1 * | 2/2004 | Hjorth | A61F 13/84 604/367 |
| 2006/0184150 A1 | 8/2006 | Noel | |
| 2006/0276767 A1 | 12/2006 | Ueminami et al. | |
| 2007/0049887 A1 | 3/2007 | Miura et al. | |
| 2007/0219515 A1 | 9/2007 | Marsh et al. | |
| 2007/0286894 A1 * | 12/2007 | Marsh | A61K 8/0208 424/443 |
| 2007/0298213 A1 | 12/2007 | Noda et al. | |
| 2007/0298214 A1 | 12/2007 | Noda et al. | |
| 2007/0298220 A1 | 12/2007 | Noda et al. | |
| 2007/0298667 A1 | 12/2007 | Noda et al. | |
| 2007/0298671 A1 | 12/2007 | Noda et al. | |
| 2007/0299416 A1 | 12/2007 | Noda et al. | |
| 2008/0010795 A1 | 1/2008 | Mizutani et al. | |
| 2008/0044622 A1 | 2/2008 | Noda et al. | |
| 2008/0044628 A1 | 2/2008 | Noda et al. | |
| 2008/0045915 A1 | 2/2008 | Noda et al. | |
| 2008/0085399 A1 | 4/2008 | Noda et al. | |
| 2008/0132136 A1 | 6/2008 | Uematsu et al. | |
| 2008/0200894 A1 * | 8/2008 | Gatto | A61F 13/15 604/385.01 |
| 2008/0286224 A1 * | 11/2008 | Vega | A61K 8/0208 424/78.31 |
| 2009/0209930 A1 * | 8/2009 | Hammons | A61F 13/476 604/365 |
| 2009/0221978 A1 * | 9/2009 | Gatto | A61L 15/34 604/367 |
| 2009/0282660 A1 | 11/2009 | Noda et al. | |
| 2010/0069874 A1 | 3/2010 | Noda et al. | |
| 2010/0137824 A1 | 6/2010 | Uematsu et al. | |
| 2010/0191207 A1 | 7/2010 | Oba et al. | |
| 2011/0118686 A1 * | 5/2011 | Vega | A61F 13/8405 604/367 |
| 2011/0319851 A1 | 12/2011 | Kudo et al. | |
| 2012/0045620 A1 | 2/2012 | Oba et al. | |
| 2012/0141742 A1 | 6/2012 | Yamaguchi et al. | |
| 2012/0177889 A1 | 7/2012 | Uematsu et al. | |
| 2012/0196091 A1 | 8/2012 | Mizutani et al. | |
| 2012/0226250 A1 * | 9/2012 | Sato | A61F 13/51104 604/367 |
| 2013/0034686 A1 | 2/2013 | Mitsuno | |
| 2013/0137328 A1 | 5/2013 | Mitsuno | |
| 2013/0226123 A1 | 8/2013 | Kudo et al. | |

FOREIGN PATENT DOCUMENTS

| | | |
|---|---|---|
| EP | 1362568 | 11/2003 |
| EP | 1371379 A1 | 12/2003 |
| EP | 2036521 A1 | 3/2009 |
| EP | 2433602 A1 | 3/2012 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | 02-152920 A | 6/1990 |
| JP | 2152920 A | 6/1990 |
| JP | H02-229255 | 9/1990 |
| JP | H05-154176 | 6/1993 |
| JP | H06-5614 | 1/1994 |
| JP | 6502104 A | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 | 10/1998 |
| JP | H11-512643 | 11/1999 |
| JP | 2000-510376 | 8/2000 |
| JP | 3091283 | 9/2000 |
| JP | 2000-512886 | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002528174 A | 9/2002 |
| JP | 2002537904 A | 11/2002 |
| JP | 2003-12490 A | 1/2003 |
| JP | 2003-024372 | 1/2003 |
| JP | 2003-052750 | 2/2003 |
| JP | 2004-500908 | 1/2004 |
| JP | 2004-049529 | 2/2004 |
| JP | 2004-508142 A | 3/2004 |
| JP | 2005-504591 | 2/2005 |
| JP | 2005-095759 | 4/2005 |
| JP | 2005193001 A | 7/2005 |
| JP | 2005-525134 | 8/2005 |
| JP | 2006501022 A | 1/2006 |
| JP | 2006-510456 | 3/2006 |
| JP | 2006-115996 | 5/2006 |
| JP | 2006-233405 A | 9/2006 |
| JP | 2006-255051 | 9/2006 |
| JP | 2006280526 A | 10/2006 |
| JP | 200714705 A | 1/2007 |
| JP | 2007-509695 | 4/2007 |
| JP | 2008-002034 | 1/2008 |
| JP | 2008-023311 | 2/2008 |
| JP | 2008-023365 | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 | 2/2008 |
| JP | 2008-025085 | 2/2008 |
| JP | 2008-029830 | 2/2008 |
| JP | 2008-503323 | 2/2008 |
| JP | 200825078 A | 2/2008 |
| JP | 200825079 A | 2/2008 |
| JP | 200829830 A | 2/2008 |
| JP | 2008-86504 A | 4/2008 |
| JP | 2008-138340 | 6/2008 |
| JP | 2008-144322 | 6/2008 |
| JP | 2008-529721 A | 8/2008 |
| JP | 2008529721 A | 8/2008 |
| JP | 2008229032 A | 10/2008 |
| JP | 2008229033 A | 10/2008 |
| JP | 2008237569 A | 10/2008 |
| JP | 2008-264084 | 11/2008 |
| JP | 2008-266813 | 11/2008 |
| JP | 2008-541943 | 11/2008 |
| JP | 2008-307179 | 12/2008 |
| JP | 20095767 A | 1/2009 |
| JP | 2009-030218 | 2/2009 |
| JP | 2009-201878 | 9/2009 |
| JP | 2009-297048 | 12/2009 |
| JP | 201088822 A | 4/2010 |
| JP | 2010518918 A | 6/2010 |
| JP | 2010-148708 | 7/2010 |
| JP | 2010-525862 A | 7/2010 |
| JP | 2010526629 A | 8/2010 |
| JP | 2010-285735 | 12/2010 |
| JP | 2010279568 A | 12/2010 |

(56) References Cited

FOREIGN PATENT DOCUMENTS

| | | |
|---|---|---|
| JP | 2011-038211 | 2/2011 |
| JP | 2011-074515 | 4/2011 |
| JP | 2011-080178 | 4/2011 |
| JP | 201167484 A | 4/2011 |
| JP | 201172650 A | 4/2011 |
| JP | 2011510801 A | 4/2011 |
| JP | 2011-104059 | 6/2011 |
| JP | 2011-120696 | 6/2011 |
| JP | 4693847 | 6/2011 |
| JP | 2011104001 A | 6/2011 |
| JP | 2011226010 A | 11/2011 |
| JP | 2011226011 A | 11/2011 |
| JP | 2012-050626 | 3/2012 |
| JP | 5122007 | 1/2013 |
| WO | 9301781 A1 | 2/1993 |
| WO | 94/27539 | 12/1994 |
| WO | 96/19173 | 6/1996 |
| WO | 98/55158 | 12/1998 |
| WO | 99/00093 | 1/1999 |
| WO | 99/29274 | 6/1999 |
| WO | 0024351 A1 | 5/2000 |
| WO | 01/045757 | 6/2001 |
| WO | 02/22104 A2 | 3/2002 |
| WO | 03/017900 | 3/2003 |
| WO | 03/028776 | 4/2003 |
| WO | 2004030713 A1 | 4/2004 |
| WO | 2004/058119 | 7/2004 |
| WO | 2005/044164 | 5/2005 |
| WO | 2006/009996 | 1/2006 |
| WO | 2006-130646 | 12/2006 |
| WO | 2008/072675 | 6/2008 |
| WO | 2008101163 A2 | 8/2008 |
| WO | 2008/139426 A1 | 11/2008 |
| WO | 2008139425 A1 | 11/2008 |
| WO | 2008-149771 | 12/2008 |
| WO | 2009102837 A2 | 8/2009 |
| WO | 2012/133724 | 10/2012 |

OTHER PUBLICATIONS

International Search Report dated Jul. 3, 2012 in corresponding International Application No. PCT/JP2012/058499.
International Search Report dated Mar. 19, 2013 in corresponding International Application No. PCT/JP2012/082087.
International Search Report dated Mar. 12, 2013 in corresponding International Application No. PCT/JP2012/082104.
International Search Report dated Mar. 19, 2013 in corresponding International Application No. PCT/JP2013/054382.
International Search Report dated May 21, 2014 in corresponding International Application No. PCT/JP2013/054796.
International Search Report dated Jul. 2, 2013 in corresponding International Application No. PCT/JP2013/058860.
International Search Report dated Jul. 2, 2013 in corresponding International Application No. PCT/JP2013/058861.
International Search Report dated Mar. 19, 2013 in corresponding International Application No. PCT/JP2012/082078.
International Search Report dated Jul. 2, 2013 in corresponding International Application No. PCT/JP2013/058862.
International Search Report dated Jun. 18, 2013 in corresponding International Application No. PCT/JP2013/058855.
International Search Report dated May 14, 2013 in corresponding International Application No. PCT/JP2013/058836.
International Search Report dated May 21, 2013 in corresponding International Application No. PCT/JP2013/058859.
Atsushi Fujita, "Prediction of Organic Compounds and Organic Conceptual Diagram", Kagaku no Ryoiki (Region of Chemistry), Oct. 1957, p. 719-725, vol. 11, No. 10.
International Search Report dated Mar. 26, 2013, corresponds to International Application No. PCT/JP2012/082977.
International Search Report dated Jan. 8, 2013, corresponds to International Application No. PCT/JP2012/075583.
International Search Report dated Jul. 17, 2012, corresponds to International Application No. PCT/JP2012/061505.
Corresponding International Application No. PCT/JP2012/058499 Search Report and Written Opinion dated Jul. 3, 2012.
Corresponding International Application No. PCT/JP2012/058499 Reply to Written Opinion dated Jan. 30, 2013.
Izuru Shinmura, "[KAISHITSU/reforming]" description of the term in Koujien, 6th edition, 6th impression, Iwanami Shoten, 2016, p. 460, Tokyo, Japan.

* cited by examiner

200 μm (a)

50μm (b)

50μm

ABSORBENT ARTICLE WITH BLOOD MODIFYING AGENT

RELATED APPLICATIONS

The present application is based on and claims priority to Application Number PCT/JP2012/058499, filed Mar. 23, 2012, Japanese Application Number 2011-079446, filed Mar. 31, 2011, and Japanese Application Number 2011-192144, filed Sep. 2, 2011, the disclosure of which is hereby incorporated by reference herein in its entirety.

TECHNICAL FIELD

The present disclosure relates to an absorbent article.

BACKGROUND ART

As the basic performance of absorbent articles such as, sanitary napkins and panty liners has continued to improve with technological developments over many years, leakage after absorption of excreta such as, menstrual blood has become a less frequent occurrence than in the past. Recent developments are now directed towards absorbent articles with even higher performance, including a feel similar to underwear, and smoothness of the top sheet even after absorption of excreta such as, menstrual blood. Menstrual blood during menstruation, in particular, can also contain components of the endometrium which are highly viscous, and the top sheet should be smooth and stick-free even after absorption of such highly viscous menstrual blood. Highly viscous menstrual blood usually remains on the top sheet in the form of masses, generally leaving the user with a visually unpleasant image, and therefore from this viewpoint as well it is preferred for no highly viscous menstrual blood to remain on the top sheet.

PTL 1, for example, describes an absorbent article that includes cellulose-based hydrophilic fiber comprising one or more surfactants selected from the group consisting of sugar alkyl ethers and sugar fatty acid esters, at locations other than the skin contact surface.

Also, PTL 2 discloses an absorbent article having a polypropyleneglycol material-containing a lotion composition on the inner surface of the top sheet (the clothing side surface), the inner surface of the back sheet (the body side surface), and on the base material between the inner surface of the top sheet and the inner surface of the back sheet.

Furthermore, PTL 3 discloses an absorbent article wherein a polypropyleneglycol material-containing lotion composition is applied on the outer surface of the top sheet (body side surface).

CITATION LIST

Patent Literature

PTL 1 Japanese Unexamined Patent Publication No. 2008-029830
PTL 2 Japanese Unexamined Patent Publication No. 2010-518918
PTL 3 WO2009/102837

SUMMARY OF INVENTION

Technical Problem

According to PTL 1, however, the inventors have noted that it is attempted to use a "surfactant" to alter the viscosity and surface tension of highly viscous menstrual blood and increase the liquid absorption rate, but the effect might not be adequate, and it might not be possible to obtain a smooth feel on the top sheet without a sticky feel, after highly viscous menstrual blood has been absorbed. Moreover, according to PTL 1, it might be necessary to coat the surfactant as an aqueous solution, and therefore problems might arise from the viewpoint of productivity when a subsequent drying step is included.

When the present inventors confirmed the effects of described in PTLs 2 and 3, it was found that the polypropyleneglycol material has different absorbing power depending on molecular weight thereof, and that with low-molecular-weight polypropyleneglycol materials, a sticky feel remains and blood redness tends to remain on the top sheet after absorption of blood. It was also found that with high molecular weight polypropyleneglycol materials, the tack of the material tends to result in a sticky feel.

It is therefore an object of the present disclosure to provide an absorbent article without a sticky feel on the top sheet and with a smooth top sheet, even after highly viscous menstrual blood has been absorbed.

It is another object of the disclosure to provide an absorbent article that is resistant to residue of highly viscous menstrual blood on the top sheet, and that does not tend to leave the wearer with a visually unpleasant image.

Solution to Problem

As a result of diligent research directed toward solving the problems described above, the present inventors have found that the problems can be solved by an absorbent article comprising a liquid-permeable top sheet, a liquid-impermeable back sheet and an absorbent body between the liquid-permeable top sheet and liquid-impermeable back sheet, wherein the liquid-permeable top sheet comprises a blood modifying agent with an IOB of 0.00-0.60, a melting point of no higher than 45° C., a water solubility of 0.00-0.05 g in 100 g of water at 25° C., and a weight-average molecular weight of less than 1,000.

Advantageous Effects of Invention

The absorbent article of the disclosure allows menstrual blood to migrate rapidly from the top sheet to the absorbent body, and therefore highly viscous menstrual blood does not easily remain on the top sheet, and the top sheet has a smooth feel without stickiness.

The absorbent article of the disclosure is resistant to highly viscous menstrual blood masses remaining on the top sheet, and does not tend to leave the user with a visually unpleasant image.

DESCRIPTION OF EMBODIMENTS

Figure 1:
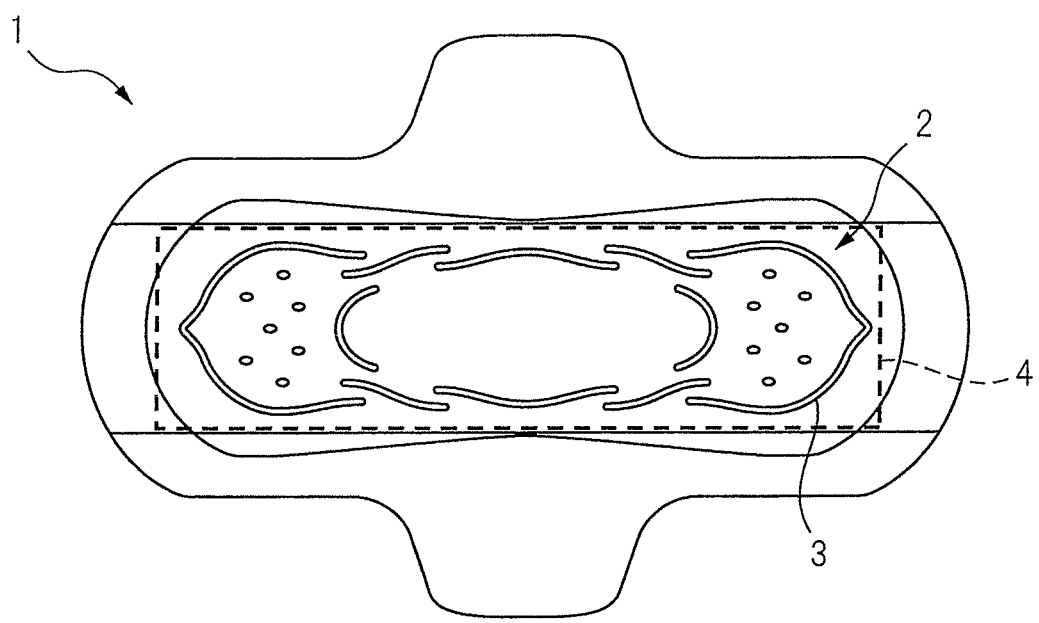
FIG. 1 is a plan view of Example 1, showing the region of the top sheet containing the blood modifying agent.

The absorbent article of this disclosure will now be explained in detail.

[Blood Modifying Agent]

The blood modifying agent of this disclosure has an IOB of about 0.00-0.60, a melting point of no higher than about 45° C., a water solubility of about 0.00-0.05 g at 25° C., and a weight-average molecular weight of less than about 1,000.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725 which is incorporated by reference herein.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO)— | 65 | 0 |
| —COOR | 60 | 0 |
| —O— | 20 | 0 |
| Triple bond | 3 | 0 |
| Double bond | 2 | 0 |
| CH$_2$ | 0 | 20 |
| iso-branch | 0 | −10 |
| tert-branch | 0 | −20 |
| Light metal (salt) | ≥500 | 0 |
| Heavy metal (salt), amine, NH$_3$ salt | ≥400 | 0 |

For example, in the case of an ester of tetradecanoic acid which has 14 carbon atoms and dodecyl alcohol which has 12 carbon atoms, the organic value is 520 (CH$_2$, 20×26) and the inorganic value is 60 (—COOR, 60×1), and therefore IOB=0.12.

In the blood modifying agent, the IOB is about 0.00-0.60, preferably about 0-0.50, more preferably about 0-0.40 and even more preferably about 0-0.30. This is because a lower IOB is associated with higher organicity and higher affinity with blood cells.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood modifying agent has a melting point of no higher than about 45° C., it may be either liquid or solid at room temperature, or in other words, the melting point may be either about 25° C. or higher or below about 25° C., and for example, it may have a melting point of about −5° C. or about −20° C. The reason for a melting point of no higher than about 45° C. for the blood modifying agent will be explained below.

The blood modifying agent does not have a lower limit for the melting point, but the vapor pressure is preferably low. The vapor pressure of the blood modifying agent is preferably about 0.00-0.01 Pa, more preferably about 0.000-0.001 Pa and even more preferably about 0.0000-0.0001 Pa, at 1 atmosphere, 25° C. Considering that the absorbent article of this disclosure is to be used in contact with the human body, the vapor pressure is preferably about 0.00-0.01 Pa, more preferably about 0.000-0.001 Pa and even more preferably about 0.0000-0.0001 Pa, at 1 atmosphere, 40° C. If the vapor pressure is high, gasification may occur during storage and the amount of blood modifying agent may be reduced, and may create problems such as, odor during wear.

The melting point of the blood modifying agent may also differ depending on the weather or duration of wear. For example, in regions with a mean atmospheric temperature of no higher than about 10° C., using a blood modifying agent with a melting point of no higher than about 10° C. may allow the blood modifying agent to stably modify blood after excretion of menstrual blood, even if it has been cooled by the ambient temperature.

Also, when the absorbent article is used for a prolonged period of time, the melting point of the blood modifying agent is preferably at the high end of the range of no higher than about 45° C. This is because the blood modifying agent is not easily affected by sweat or friction during wearing, and will not easily migrate even during prolonged wearing.

The water solubility of 0.00-0.05 g may be measured by adding 0.05 g of sample to 100 g of deionized water at 25° C., allowing it to stand for 24 hours, and gently stirring if necessary, and then visually evaluating whether or not the sample has dissolved.

As used herein, the term "solubility" in regard to water solubility includes cases where the sample completely dissolves in deionized water to form a homogeneous mixture, and cases where the sample is completely emulsified. As used herein, "completely" means that no mass of the sample remains in the deionized water.

In the above described art, top sheet surfaces are coated with surfactants in order to alter the surface tension of blood and promote rapid absorption of blood. However, because surfactants generally have high water solubility, the surfactant-coated top sheet is highly miscible with hydrophilic components (such as, blood plasma) in the blood and therefore, instead, they tend to cause residue of blood on the top sheet. The aforementioned blood modifying agent has low water solubility and therefore, unlike the surfactants used in the above described art, it does not cause residue of blood on the top sheet and allows rapid migration into the absorbent body.

As used herein, water solubility in 100 g of water at 25° C. may be simply referred to as "water solubility".

The blood modifying agent may have a water solubility of approximately 0.00 g. Therefore, the lower limit for the water solubility in the blood modifying agent is approximately 0.00 g.

The blood modifying agent has a weight-average molecular weight of less than about 1,000 and preferably a weight-average molecular weight of less than about 900. This is because, if the weight-average molecular weight is about 1,000 or greater, tack may result in the blood modifying agent itself, tending to create a feeling of unpleasantness for the wearer. Also, a high weight-average molecular weight will tend to result in high viscosity of the blood modifying agent, and it will be difficult to lower the viscosity of the blood modifying agent by heating, to a viscosity suitable for coating. As a result, it will sometimes be necessary to dilute the blood modifying agent with a solvent.

The blood modifying agent preferably has a weight-average molecular weight of about 100 or greater, and more preferably it has a weight-average molecular weight of about 200 or greater. This is because if the weight-average molecular weight is low, the vapor pressure may be increased, gasification may occur during storage and the amount of blood modifying agent may be reduced, and may create problems such as, odor during wear.

As used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w=\Sigma N_i M_i^2/\Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 μL
Detection: RI (differential refractometer)

The weight-average molecular weights listed in the examples of the present specification were measured under the conditions described below.

Preferably, the blood modifying agents is selected from the group consisting of following items (i)-(iii), and any combination thereof:

(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting a hydrogen of the hydrocarbon moiety.

As used herein, "hydrocarbon" refers to a compound composed of carbon and hydrogen, and it may be a chain hydrocarbon, such as, a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as, aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are more preferred than compounds in which at least one hydrogen on the hydrocarbon moiety is substituted with a carboxyl group (—COOH). As shown in Table 1, the carboxyl groups bond with metals and the like in menstrual blood, drastically increasing the inorganic value from 150 to 400 or greater, and therefore a blood modifying agent with carboxyl groups can increase the IOB value to more than about 0.60 during use, potentially lowering the affinity with blood cells.

More preferably, the blood modifying agent is selected from the group consisting of following items (i')-(iii'), and any combination thereof:

(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety.

When 2 or more same or different bonds are inserted in the compound of (ii') or (iii'), i.e., when 2 or more bonds each selected from the group consisting of carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood modifying agent is more preferably a compound with no more than about 1.8 carbonyl bonds (—CO—), no more than 2 ester bonds (—COO—), no more than about 1.5 carbonate bonds (—OCOO—), no more than about 6 ether bonds (—O—), no more than about 0.8 carboxyl groups (—COOH) and/or no more than about 1.2 hydroxyl groups (—OH), per 10 carbon atoms in the hydrocarbon moiety.

Even more preferably, the blood modifying agent is selected from the group consisting of following items (A)-(F), and any combination thereof:

(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;
(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;
(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;

(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

The blood modifying agent in accordance with (A) to (F) will now be described in detail.

[(A) Ester of (A1) a Compound Having a Chain Hydrocarbon Moiety and 2-4 Hydroxyl Groups Substituting Hydrogens on the Chain Hydrocarbon Moiety, and (A2) a Compound Having a Chain Hydrocarbon Moiety and 1 Carboxyl Group Substituting a Hydrogen on the Chain Hydrocarbon Moiety]

The (A) ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety (hereunder also referred to as "compound (A)") is not necessary for all of the hydroxyl groups to be esterified so long as the IOB, melting point and water solubility are within the aforementioned ranges.

Examples of (A1) a compound having a chain hydrocarbon moiety and 2-4 hydroxyl groups substituting hydrogens on the chain hydrocarbon moiety (hereunder also referred to as "compound (A1)") include chain hydrocarbon tetraols such as, alkanetetraols, including pentaerythritol, chain hydrocarbon triols such as, alkanetriols, including glycerins, and chain hydrocarbon diols such as alkanediols, including glycols.

Examples of (A2) a compound having a chain hydrocarbon moiety and 1 carboxyl group substituting a hydrogen on the chain hydrocarbon moiety (hereunder also referred to as "compound (A2)") include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Ester of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

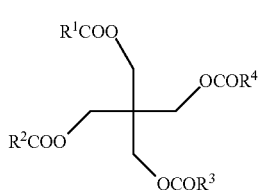

(1)

triesters of pentaerythritol and fatty acids, represented by the following formula (2):

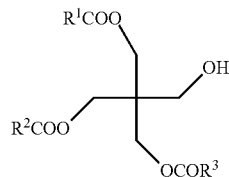

(2)

diesters of pentaerythritol and fatty acids, represented by the following formula (3):

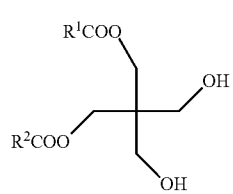

(3)

and monoesters of pentaerythritol and fatty acids, represented by the following formula (4).

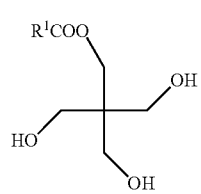

(4)

In the formulas, $R^1$-$R^4$ each represent a chain hydrocarbon.

The fatty acids composing the esters of pentaerythritol and fatty acids ($R^1COOH$, $R^2COOH$, $R^3COOH$, and $R^4COOH$) are not particularly restricted as long as the pentaerythritol and fatty acid esters satisfy the conditions for the IOB, melting point and water solubility, and for example, there may be mentioned saturated fatty acids, such as $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and isomers thereof such as, 2-methylpropanoic acid ($C_4$), pentanoic acid ($C_5$) and isomers thereof such as, 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as, 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$) and triacontanoic acid ($C_{30}$), as well as isomers of the foregoing (excluding those mentioned above).

The fatty acid may also be an unsaturated fatty acid. Examples of unsaturated fatty acids include $C_3$-$C_{20}$ unsaturated fatty acids, such as, monounsaturated fatty acids including crotonic acid ($C_4$), myristoleic acid ($C_{14}$), palmitoleic acid ($C_{16}$), oleic acid ($C_H$), elaidic acid ($C_H$), vaccenic acid ($C_H$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as, α-linolenic acid ($C_{18}$) and γ-linolenic acid ($C_{18}$), pinolenic acid ($C_{18}$), eleostearic acids, such as, α-eleostearic acid ($C_{18}$) and β-eleostearic acid ($C_{18}$), Mead acid ($C_H$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, in order to lower the IOB and result in greater hydrophobicity, the ester of pentaerythritol and a fatty acid is preferably a diester, triester or tetraester, more preferably a triester or tetraester, and even more preferably a tetraester.

In a tetraester of pentaerythritol and a fatty acid, the IOB is 0.60 if the total number of carbons of the fatty acid composing the tetraester of the pentaerythritol and fatty acid, i.e., the total number of carbons of the $R^1C$, $R^2C$, $R^3C$ and $R^4C$ portions in formula (1), is 15. Thus, when the total number of carbons of the fatty acid composing the tetraester of the pentaerythritol and fatty acid is approximately 15 or greater, the IOB satisfies the condition of being within about 0.00 to 0.60.

Examples of tetraesters of pentaerythritol and fatty acids include tetraesters of pentaerythritol with hexanoic acid ($C_6$), heptanoic acid ($C_7$), octanoic acid ($C_8$) such as, 2-ethylhexanoic acid ($C_8$), nonanoic acid ($C_9$), decanoic acid ($C_{10}$) and/or dodecanoic acid ($C_{12}$).

In a triester of pentaerythritol and a fatty acid, the ICE is 0.58 if the total number of carbons of the fatty acid composing the triester of the pentaerythritol and fatty acid, i.e., the total number of carbons of the $R^1C$, $R^2C$ and $R^3C$ portions in formula (2), is 19. Thus, when the total number of carbons of the fatty acid composing the triester of the pentaerythritol and fatty acid is approximately 19 or greater, the IOB satisfies the condition of being within about 0.00 to 0.60.

In a diester of pentaerythritol and a fatty acid, the IOB is 0.59 if the total number of carbons of the fatty acid composing the diester of the pentaerythritol and fatty acid, i.e., the total number of carbons of the $R^1C$ or $R^2C$ portion in formula (3), is 22. Thus, when the total number of carbons of the fatty acid composing the diester of the pentaerythritol and fatty acid is approximately 22 or greater, the IOB satisfies the condition of being within about 0.00 to 0.60.

In a monoester of pentaerythritol and a fatty acid, the IOB is 0.60 if the number of carbons of the fatty acid composing the monoester of the pentaerythritol and fatty acid, i.e., the number of carbons of the $R^1C$ portion in formula (4), is 25. Thus, when the number of carbons of the fatty acid composing the monoester of the pentaerythritol and fatty acid is approximately 25 or greater, the IOB satisfies the condition of being within about 0.00 to 0.60.

The effects of double bonds, triple bonds, iso-branches and tert-branches are not considered in this calculation.

Commercial products which are esters of pentaerythritol and fatty acids include UNISTAR H-408BRS and H-2408BRS-22 (mixed product) (both products of NOF Corp.).

[($a_2$) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

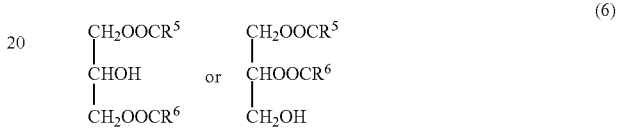

and monoesters of glycerin and fatty acids, represented by the following formula (7):

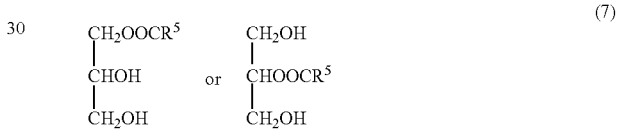

wherein $R^5$-$R^7$ each represent a chain hydrocarbon.

The fatty acid composing the ester of glycerin and a fatty acid ($R^5COOH$, $R^6COOH$ and $R^7COOH$) is not particularly restricted so long as the ester of glycerin and a fatty acid satisfies the conditions for the IOB, melting point and water solubility, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, in order to lower the IOB and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_H$), triesters of glycerin with octanoic acid ($C_8$), decanoic acid ($C_H$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of no higher than about 45° C., preferred triesters of glycerin and fatty acids are those with no more than about 40 as the total number of carbons of the fatty acid composing the triester of glycerin and the fatty acid, i.e., the total number of carbons of the $R^5C$, $R^6C$ and $R^7C$ sections in formula (5).

In a triester of glycerin and a fatty acid, the IOB value is 0.60 when the total number of carbons of the fatty acid composing the triester of glycerin and the fatty acid, i.e., the total number of carbons of the $R^5C$, $R^6C$ and $R^7C$ portions in formula (5), is 12. Thus, when the total number of carbons of the fatty acid composing the triester of the glycerin and fatty acid is approximately 12 or greater, the IOB satisfies the condition of being within about 0.00 to 0.60.

Triesters of glycerin and fatty acids, being aliphatic and therefore potential constituent components of the human body are preferred from the viewpoint of safety.

Commercial products of triesters of glycerin and fatty acids include tri-coconut fatty acid glycerides, NA36, PAN-ACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

In a diester of glycerin and a fatty acid, the IOB is 0.58 if the total number of carbons of the fatty acid composing the diester of the glycerin and fatty acid, i.e., the total number of carbons of the $R^5C$ and $R^6C$ portions in formula (6), is 16. Thus, when the total number of carbons of the fatty acid composing the diester of the glycerin and fatty acid is approximately 16 or greater, the IOB satisfies the condition of being about 0.00 to 0.60.

Monoesters of glycerin and fatty acids are also known as monoglycerides, and examples include glycerin and octadecanoic acid ($C_{18}$) monoester, and glycerin and docosanoic acid ($C_{22}$) monoester.

In a monoester of glycerin and a fatty acid, the IOB is 0.59 if the number of carbons of the fatty acid composing the monoester of the glycerin and fatty acid, i.e., the number of carbons of the $R^5C$ portion in formula (7), is 19. Thus, when the number of carbons of the fatty acid composing the monoester of the glycerin and fatty acid is approximately 19 or greater, the IOB satisfies the condition of being about 0.00 to 0.60.

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as, $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

$$R^8COOC_kH_{2k}OCOR^9 \quad (8)$$

wherein k represents an integer of 2-6, and $R^8$ and $R^9$ each represent a chain hydrocarbon,
and monoesters of $C_2$-$C_6$ glycols and fatty acids, represented by the following formula (9):

$$R^8COOC_kH_{2k}OH \quad (9)$$

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the IOB, melting point and water solubility, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

In a diester of butylene glycol (k=4) and a fatty acid represented by formula (8), IOB is 0.60 when the total number of carbons of the $R^8C$ and $R^9C$ portions is 6. Thus, when the total number of carbon atoms in a diester of butylene glycol (k=4) and a fatty acid represented by formula (8) is approximately 6 or greater, the IOB satisfies the condition of being about 0.00-0.60. In a monoester of ethylene glycol (k=2) and a fatty acid represented by formula (9), IOB is 0.57 when the number of carbons of the $R^8C$ portion is 12. Thus, when the total number of carbon atoms in the fatty acid composing a monoester of ethylene glycol (k=2) and a fatty acid represented by formula (9) is approximately 12 or greater, the IOB satisfies the condition of being about 0.00-0.60.

Considering the potential for degradation by oxidation and the like, the ester of the $C_2$-$C_6$ glycol and fatty acid is preferably a $C_2$-$C_6$ glycol and fatty acid ester, which is derived from a saturated fatty acid, i.e., an ester of a $C_2$-$C_6$ glycol and a saturated fatty acid.

Also, in order to lower the IOB and result in greater hydrophobicity, the ester of the $C_2$-$C_6$ glycol and fatty acid is preferably a glycol and fatty acid ester derived from a glycol with a greater number of carbons, such as, an ester of a glycol and a fatty acid derived from butylene glycol, pentylene glycol or hexylene glycol.

Also, in order to lower the IOB and obtain in greater hydrophobicity, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting Hydrogens on the Chain Hydrocarbon Moiety and (B2) a Compound Having a Chain Hydrocarbon Moiety and 1 Hydroxyl Group Substituting a Hydrogen on the Chain Hydrocarbon Moiety]

The (B) ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety (hereunder also referred to as "compound (B)") is not necessary for all of the hydroxyl groups to be etherified as long as the IOB, melting point and water solubility are within the aforementioned ranges.

Examples of (B1) a compound having a chain hydrocarbon moiety and 2-4 hydroxyl groups substituting hydrogens on the chain hydrocarbon moiety (hereunder also referred to as "compound (B1)") include those mentioned for "compound (A)" as compound (A1), such as, pentaerythritol, glycerin and glycol.

Examples of (B2) a compound having a chain hydrocarbon moiety and 1 hydroxyl group substituting a hydrogen on the chain hydrocarbon moiety (hereunder also referred to as "compound (B2)") include compounds wherein 1 hydrogen on the hydrocarbon is substituted with 1 hydroxyl group (—OH), such as, aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as, methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol ($C_4$), pentyl alcohol ($C_5$), hexyl alcohol ($C_6$), heptyl alcohol ($C_7$), octyl alcohol (CO and isomers thereof, including 2-ethylhexyl alcohol ($C_8$), nonyl alcohol ($C_9$), decyl alcohol ($C_H$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C=C double bond, such as, oleyl alcohol, and for example, these are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohols, such as, monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as, monoethers, diethers and triethers, preferably diethers and triethers and more preferably triethers, and ($b_3$) an ether of a chain hydrocarbon diol and at least one aliphatic monohydric alcohol, such as, monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

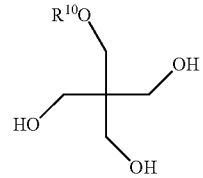
(10)

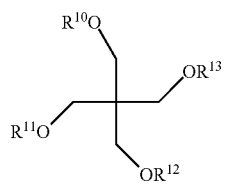
(11)

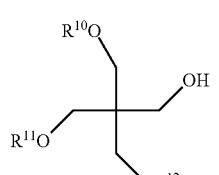
(12)

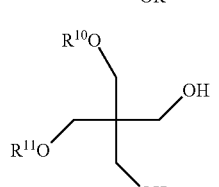
(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

$$\begin{array}{l} CH_2OR^{14} \\ CHOR^{15} \\ CH_2OR^{16} \end{array} \quad (14)$$

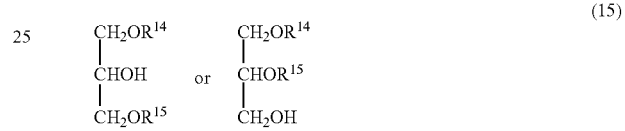
(15)

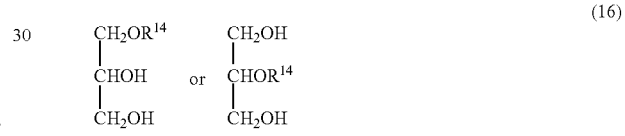
(16)

wherein $R^{14}$-$R^{16}$ each represent a chain hydrocarbon.

Examples of an ether of a chain hydrocarbon diol and at least one aliphatic monohydric alcohols include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

In the tetraether of pentaerythritol and an aliphatic monohydric alcohol, the IOB is 0.44 when the total number of carbon atoms of the aliphatic monohydric alcohol composing the tetraether of pentaerythritol and the aliphatic monohydric alcohol, i.e., the total number of carbon atoms of the $R^{10}$, $R^{11}$, $R^{12}$ and $R^{13}$ portions in formula (10), is 4. Thus, when the total number of carbon atoms of the aliphatic monohydric alcohol composing a tetraether of pentaerythritol and an aliphatic monohydric alcohol is approximately 4 or greater, the IOB value satisfies the condition of being within about 0.00 to 0.60.

In the triether of pentaerythritol and an aliphatic monohydric alcohol, the IOB is 0.57 when the total number of carbon atoms of the aliphatic monohydric alcohol composing the triether of pentaerythritol and the aliphatic monohydric alcohol, i.e., the total number of carbon atoms of the $R^{10}$, $R^{11}$ and $R^{12}$ portions in formula (11), is 9. Thus, when the total number of carbon atoms of the aliphatic monohydric alcohol composing a triether of pentaerythritol and an aliphatic monohydric alcohol is approximately 9 or greater, the IOB value satisfies the condition of being within about 0.00 to 0.60.

In the diether of pentaerythritol and an aliphatic monohydric alcohol, the IOB is 0.60 when the total number of carbon atoms of the aliphatic monohydric alcohol composing the diether of pentaerythritol and the aliphatic monohydric alcohol, i.e., the total number of carbon atoms of the $R^{10}$ and $R^{11}$ portions in formula (12), is 15. Thus, when the total number of carbon atoms of the aliphatic monohydric alcohol composing a diether of pentaerythritol and an aliphatic monohydric alcohol is approximately 15 or greater, the IOB value satisfies the condition of being within about 0.00 to 0.60.

In the monoether of pentaerythritol and an aliphatic monohydric alcohol, the IOB is 0.59 when the number of carbon atoms of the aliphatic monohydric alcohol composing the monoether of pentaerythritol and the aliphatic monohydric alcohol, i.e., the number of carbon atoms of the $R^{10}$ portion in formula (13), is 22. Thus, when the number of carbon atoms of the aliphatic monohydric alcohol composing a monoether of pentaerythritol and an aliphatic monohydric alcohol is approximately 22 or greater, the IOB value satisfies the condition of being within about 0.00 to 0.60.

In the triether of glycerin and an aliphatic monohydric alcohol, the IOB is 0.50 when the total number of carbon atoms of the aliphatic monohydric alcohol composing the triether of glycerin and the aliphatic monohydric alcohol, i.e., the total number of carbon atoms of the $R^{14}$, $R^{15}$ and $R^{16}$ portions in formula (14), is 3. Thus, when the total number of carbon atoms of the aliphatic monohydric alcohol composing a triether of glycerin and an aliphatic monohydric alcohol is approximately 3 or greater, the IOB value satisfies the condition of being within about 0.00 to 0.60.

In the diether of glycerin and an aliphatic monohydric alcohol, the IOB is 0.58 when the total number of carbon atoms of the aliphatic monohydric alcohol composing the diether of glycerin and the aliphatic monohydric alcohol, i.e., the total number of carbon atoms of the $R^{14}$ and $R^{15}$ portions in formula (15), is 9. Thus, when the total number of carbon atoms of the aliphatic monohydric alcohol composing a diether of glycerin and an aliphatic monohydric alcohol is approximately 9 or greater, the IOB value satisfies the condition of being within about 0.00 to 0.60.

In the monoether of glycerin and an aliphatic monohydric alcohol, the IOB is 0.58 when the number of carbon atoms of the aliphatic monohydric alcohol composing the monoether of glycerin and the aliphatic monohydric alcohol, i.e., the number of carbon atoms of the $R^{14}$ portion in formula (16), is 16. Thus, when the number of carbon atoms of the aliphatic monohydric alcohol composing a monoether of glycerin and an aliphatic monohydric alcohol is approximately 16 or greater, the IOB value satisfies the condition of being within about 0.00 to 0.60.

In a diether of butylene glycol (n=4) and aliphatic monohydric alcohol represented by formula (17), the IOB is 0.33 when the total number of carbon atoms of the $R^{17}$ and $R^{18}$ portions is 2. Thus, when the number of carbon atoms of the aliphatic monohydric alcohol composing a diether of butylene glycol (n=4) and an aliphatic monohydric alcohol represented by formula (17) is approximately 2 or greater, the IOB value satisfies the condition of being within about 0.00 to 0.60. Also, in a monoether of ethylene glycol (n=2) and aliphatic monohydric alcohol represented by formula (18), the IOB is 0.60 when the number of carbon atoms of the $R^{17}$ portion is 8. Thus, when the number of carbon atoms of the aliphatic monohydric alcohol in a monoether of ethylene glycol (n=2) and an aliphatic monohydric alcohol represented by formula (18) is approximately 8 or greater, the IOB value satisfies the condition of being within about 0.00 to 0.60.

Compound (B) may be produced by dehydrating condensation of compound (B1) and compound (B2), in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting Hydrogens on the Chain Hydrocarbon Moiety and (C2) a Compound Having a Chain Hydrocarbon Moiety and 1 Hydroxyl Group Substituting a Hydrogen on the Chain Hydrocarbon Moiety]

The (C) ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety (hereunder also referred to as "compound (C)") is not necessary for all of the carboxyl groups to be esterified so long as the IOB, melting point and water solubility are within the aforementioned ranges.

Examples of (C1) a carboxylic acid, hydroxy acid, alkoxy acid or oxoacid comprising a chain hydrocarbon moiety and 2-4 carboxyl groups substituting hydrogens on the chain hydrocarbon moiety (hereunder also referred to as "compound (C1)") include chain hydrocarbon carboxylic acids with 2-4 carboxyl groups, such as, chain hydrocarbon dicarboxylic acids including alkanedicarboxylic acids such as, ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids such as, propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids such as, butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as, malic acid, tartaric acid, citric acid and isocitric acid, chain hydrocarbon alkoxy acids with 2-4 carboxyl groups, such as, O-acetylcitric acid, and chain hydrocarbon oxoacids with 2-4 carboxyl groups.

(C2) Compound having a chain hydrocarbon moiety and 1 hydroxyl group substituting a hydrogen on the chain hydrocarbon moiety includes those mentioned for "compound (B)", such as, aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of aliphatic monohydric alcohols and aliphatic monohydric alcohols include compounds having the following formula (19):

$$R^{19}OR^{20} \qquad (19)$$

wherein $R^{19}$ and $R^{20}$ each represent a chain hydrocarbon.

The aliphatic monohydric alcohol composing the ether (corresponding to $R^{19}OH$ and $R^{20}OH$ in formula (19)) is not particularly restricted so long as the ether satisfies the conditions for the IOB, melting point and water solubility, and for example, it may be one of the aliphatic monohydric alcohols mentioned for "compound (B)".

In an ether of an aliphatic monohydric alcohol and an aliphatic monohydric alcohol, the IOB is 0.50 when the total number of carbon atoms of the aliphatic monohydric alcohols composing the ether, i.e., the total number of carbons of the $R^{19}$ and $R^{20}$ portions in formula (19), is 2, and therefore when the total number of carbons of the aliphatic monohydric alcohols composing the ether is about 2 or greater, this condition for the IOB is satisfied. However, when the total number of carbons of the aliphatic monohydric alcohols composing the ether is about 6, the water solubility is as high as about 2 g, which is problematic from the viewpoint of vapor pressure as well. In order to satisfy the condition of a water solubility of about 0.00-0.05 g, the total number of carbons of the aliphatic monohydric alcohols composing the ether is preferably about 8 or greater.

[($d_2$) Dialkyl Ketone]

The dialkyl ketone may be a compound of the following formula (20):

$$R^{21}COR^{22} \qquad (20)$$

wherein $R^{21}$ and $R^{22}$ are each an alkyl group.

In a dialkyl ketone, the IOB is 0.54 when the total number of carbon atoms of $R^{21}$ and $R^{22}$ is 5, and therefore this condition for the IOB is satisfied if the total number of carbons is about 5 or greater. However, when the total number of carbons of dialkyl ketone is about 5, the water solubility is as high as about 2 g. Therefore, in order to satisfy the condition of a water solubility of about 0.00-0.05 g, the total number of carbons of dialkyl ketone is preferably about 8 or greater. In consideration of vapor pressure, the number of carbon atoms of dialkyl ketone is preferably about 10 or greater and more preferably about 12 or greater.

If the total number of carbon atoms of dialkyl ketone is about 8, such as, in 5-nonanone, for example, the melting point is approximately −50° C. and the vapor pressure is about 230 Pa at 20° C.

The dialkyl ketone may be a commercially available product, or it may be obtained by a known method, such as, by oxidation of a secondary alcohol with chromic acid or the like.

[($d_3$) Ester of a Fatty Acid and an Aliphatic Monohydric Alcohol]

Examples of esters of fatty acids and aliphatic monohydric alcohols include compounds having the following formula (21):

$$R^{23}COOR^{24} \qquad (21)$$

wherein $R^{23}$ and $R^{24}$ each represent a chain hydrocarbon.

Examples of fatty acids composing these esters (corresponding to $R^{23}COOH$ in formula (21)) include the fatty acids mentioned for the "($a_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol composing the ester (corresponding to $R^{24}OH$ in formula (21)) may be one of the aliphatic monohydric alcohols mentioned for "compound (B)".

In an ester of such a fatty acid and aliphatic monohydric alcohol, the IOB is 0.60 when the total number of carbon atoms of the fatty acid and aliphatic monohydric alcohol, i.e., the total number of carbon atoms of the $R^{23}C$ and $R^{24}$ portion in formula (21), is 5, and therefore this condition for the IOB is satisfied when the total number of carbon atoms of the $R^{23}C$ and $R^{24}$ portion is about 5 or greater. However, with butyl acetate in which the total number of carbon atoms is 6, the vapor pressure is high at greater than 2000 Pa. In consideration of vapor pressure, therefore, the total number of carbon atoms is preferably about 12 or greater. If the total number of carbon atoms is about 11 or greater, it will be possible to satisfy the condition of a water solubility of about 0.00-0.05 g.

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \qquad (22)$$

wherein $R^{25}$ and $R^{26}$ are each an alkyl group.

In a dialkyl carbonate, the IOB is 0.57 when the total number of carbon atoms of $R^{25}$ and $R^{26}$ is 6, and therefore this condition for the IOB is satisfied if the total number of carbons of $R^{25}$ and $R^{26}$ is about 6 or greater.

In consideration of water solubility, the total number of carbon atoms of $R^{25}$ and $R^{26}$ is preferably about 7 or greater and more preferably about 9 or greater.

The dialkyl carbonate may be a commercially available product, or it may be synthesized by reaction between phosgene and an alcohol, reaction between formic chloride and an alcohol or alcoholate, or reaction between silver carbonate and an alkyl iodide.

[(E) Polyoxy $C_3$-$C_6$ Alkylene Glycol, or Alkyl Ester or Alkyl Ether Thereof]

The (E) polyoxy $C_3$-$C_6$ alkylene glycol, or alkyl ester or alkyl ether thereof (hereunder also referred to as "compound (E)") may be ($e_1$) a polyoxy $C_3$-$C_6$ alkylene glycol, ($e_2$) an ester of a polyoxy $C_3$-$C_6$ alkylene glycol and at least one fatty acid, or ($e_3$) an ether of a polyoxy $C_3$-$C_6$ alkylene glycol and at least one aliphatic monohydric alcohol. These will now be explained.

[($e_1$) Polyoxy $C_3$-$C_6$ Alkylene Glycol]

Polyoxy $C_3$-$C_6$ alkylene glycols refer to i) one or more homopolymers having a unit selected from the group consisting of oxy $C_{3-6}$ alkylene units, such as, oxypropylene unit, oxybutylene unit, oxypentylene unit and oxyhexylene unit and having hydroxyl groups at both ends, ii) one or more block copolymers having 2 or more units selected from oxy $C_{3-6}$ alkylene units, such as, oxypropylene unit, oxybutylene unit, oxypentylene unit and oxyhexylene unit and having hydroxyl groups at both ends, or iii) random copolymers having 2 or more units selected from oxy $C_{3-6}$ alkylene units, such as, oxypropylene unit, oxybutylene unit, oxypentylene unit and oxyhexylene unit and having hydroxyl groups at both ends.

The polyoxy $C_3$-$C_6$ alkylene glycol is represented by the following formula (23):

$$HO\text{---}(C_mH_{2m}O)_n\text{---}H \qquad (23)$$

wherein m is an integer of 3-6.

In polyethylene glycol (corresponding to the homopolymer of formula (23) where m=2), when n≥45, the condition for IOB of about 0.00-0.60 is satisfied, but when n≥45, the weight-average molecular weight exceeds about 2,000.

Also, confirmation by the present inventors has indicated that for polypropylene glycol (corresponding to the homopolymer of formula (23) where m=3), an IOB of about 0.00-0.60, a melting point of no higher than about 45° C. and a water solubility of about 0.00-0.05 g in 100 g of water at 25° C., are satisfied only when the weight-average molecular weight is about 1,000 or greater. Thus, a polypropylene glycol homopolymer does not fall within the range of the aforementioned blood modifying agent.

Therefore, propylene glycol should be included in the ($e_1$) polyoxy $C_3$-$C_6$ alkylene glycol only as a copolymer or random polymer with another glycol.

The value of n in formula (23) is a value such that the polyoxy $C_3$-$C_6$ alkylene glycol has an IOB of about 0.00-0.60, a melting point of no higher than about 45° C. and a water solubility of about 0.00-0.05 g in 100 g of water at 25° C.

For example, when formula (23) is polybutylene glycol (homopolymer, m=4), the IOB is 0.57 when n=7. Thus, when formula (23) is polybutylene glycol (homopolymer, m=4), the condition for the IOB is satisfied when n is equal to or greater than about 7.

Examples of commercial products of polyoxy $C_3$-$C_6$ alkylene glycols include UNIOL™ PB-500 and PB-700 (both products of NOF Corp.).

[($e_2$) Ester of a Polyoxy $C_3$-$C_6$ Alkylene Glycol and at Least One Fatty Acid]

Examples of an ester of a polyoxy $C_3$-$C_6$ alkylene glycol and at least one fatty acid include the polyoxy $C_3$-$C_6$ alkylene glycols mentioned for "($e_1$) polyoxy $C_3$-$C_6$ alkylene glycol" in which one or both OH ends have been esterified with fatty acids, i.e., monoesters and diesters.

Examples of fatty acids to be esterified in the ester of a polyoxy $C_3$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

[($e_3$) Ether of a Polyoxy $C_3$-$C_6$ Alkylene Glycol and at Least One Aliphatic Monohydric Alcohol]

Examples of an ether of a polyoxy $C_3$-$C_6$ alkylene glycol and at least one aliphatic monohydric alcohol include the polyoxy $C_3$-$C_6$ alkylene glycols mentioned for "($e_1$) Polyoxy $C_3$-$C_6$ alkylene glycol" wherein one or both OH ends have been etherified by an aliphatic monohydric alcohol, i.e., monoethers and diethers.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

The chain hydrocarbon has an inorganic value of 0 and thus an IOB of 0.00, while the water solubility is also approximately 0 g, and therefore if the melting point is no higher than about 45° C., it may be included among the aforementioned blood modifying agents. Examples of such chain hydrocarbons include ($f_1$) chain alkanes, such as, linear alkanes and branched alkanes, and linear alkanes generally include those with no more than 22 carbons, in consideration of a melting point of no higher than about 45° C. In consideration of vapor pressure, they generally include those with 13 or more carbons. Branched alkanes generally include those with 22 or more carbons, since their melting points are often lower than linear alkanes, given the same number of carbon atoms.

Examples of commercially available hydrocarbon products include PARLEAM 6 (NOF Corp.).

The blood modifying agent has been found to have at least function of lowering blood viscosity and surface tension, which will be considered in detail in the examples. Menstrual blood to be absorbed by the absorbent article contains proteins of the endometrial wall, for example, unlike ordinary blood, which act to bind together blood cells, such that the blood cells form a rouleau state. The menstrual blood to be absorbed by the absorbent article therefore tends to have high viscosity, and if the top sheet is a nonwoven fabric or woven fabric, the menstrual blood becomes clogged between the fibers creating a residual sticky feel for the wearer, while the menstrual blood also diffuses on the surface of the top sheet and tends to leak.

In the absorbent article of this disclosure, the top sheet comprises a blood modifying agent which has been found to have at least function of lowering blood viscosity and surface tension, and therefore if the top sheet is a nonwoven fabric or woven fabric, clogging of menstrual blood between the top sheet fibers is reduced and menstrual blood can rapidly migrate from the top sheet to the absorbent body.

Also, in the absorbent article of this disclosure, the blood modifying agent has a melting point of no higher than about 45° C., and therefore, whether liquid or solid at ordinary temperature (25° C.), when it contacts with body fluid at approximately 30-40° C., it liquefies (or is a liquid) and readily dissolves in the body fluid.

In addition, the blood modifying agent which has an IOB of about 0.00 to 0.60 has high organicity and readily infiltrates between blood cells, and it therefore stabilizes the blood cells and can prevent formation of a rouleau structure by the blood cells.

Since the blood modifying agent stabilizes blood cells and helps to prevent formation of a rouleau structure by the blood cells, it facilitates absorption of menstrual blood by the absorbent body. For example, with an absorbent article comprising an acrylic super-absorbent polymer, or SAP, absorption of menstrual blood is known to lead to covering of the SAP surface by rouleau-formed blood cells and inhibition of the absorption performance of the SAP, but presumably stabilization of the blood cells allows the absorption performance of the SAP to be exhibited more easily. In addition, the blood modifying agent which has high affinity with erythrocytes protects the erythrocyte membranes, and therefore may minimize destruction of the erythrocytes.

Any liquid-permeable top sheet that is commonly used in the art may be employed without any particular restrictions, and for example, it may be a sheet-like material having a structure that allows permeation of liquids, such as, a porous film, woven fabric, nonwoven fabric or the like. The fibers composing such a woven fabric or nonwoven fabric may be natural fibers or chemical fibers, with examples of natural fibers including cellulose such as, ground pulp and cotton, and examples of chemical fibers including regenerated cellulose such as, rayon and fibril rayon, semi-synthetic cellulose such as, acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as, SMS and the like).

Liquid-impermeable back sheets include films comprising PE and PP, air-permeable resin films, air-permeable resin films bonded to spunbond or spunlace nonwoven fabrics, and multilayer nonwoven fabrics such as, SMS. In consideration of flexibility of the absorbent article, a low-density polyethylene (LDPE) film with a basis weight of about 15-30 g/m², for example, is preferred.

One embodiment of the absorbent article of the disclosure may comprises a second sheet between the liquid-permeable top sheet and the absorbent body. The second sheet may be any of the same examples as for the liquid-permeable top sheet.

The first example of the absorbent body is one having an absorbent core covered with a core wrap.

Examples of components for the absorbent core include hydrophilic fibers, including cellulose such as, ground pulp or cotton, regenerated cellulose such as, rayon or fibril rayon, semi-synthetic cellulose such as, acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super absorbent polymer, such as, granules of a sodium acrylate copolymer or the like.

The core wrap is not particularly restricted so long as it is a substance that is liquid-permeable and with a barrier property that does not allow permeation of the polymer absorbent, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions so long as it is one that can be used in an absorbent article such as, a sanitary napkin.

The blood modifying agent may be present at any location in the planar direction of the top sheet, such as, across the entire top sheet, or at the center region near the vaginal opening.

When the liquid-permeable top sheet is formed from a nonwoven fabric or woven fabric, the blood modifying agent preferably does not fill the voids between the fibers of the nonwoven fabric or woven fabric, and for example, the blood modifying agent may be attached as droplets or particulates on the surface of the nonwoven fabric fibers, or covering the surfaces of the fibers. On the other hand, when the liquid-permeable top sheet is formed from a porous film, the blood modifying agent preferably does not fill the holes in the porous film, and for example, the blood modifying agent may be attached as droplets or particulates on the surface of the porous film. This is because if the blood modifying agent fills the voids between the fibers of the nonwoven fabric or woven fabric, or fills the holes in the porous film, migration of the absorbed liquid into the absorbent body may be inhibited.

The blood modifying agent also preferably has a large surface area, in order to allow rapid migration into the absorbed liquid, and a blood modifying agent present as droplets or particulates preferably has a small droplet/particle size.

In an embodiment where the absorbent article has a second sheet, the second sheet may comprise a blood modifying agent. Also, according to an embodiment of the absorbent article of the present disclosure, the absorbent body may comprise a blood modifying agent.

In this absorbent article, the top sheet comprises the blood modifying agent at a basis weight in the range of preferably 1-30 g/m²; more preferably 2-20 g/m² and more preferably 3-10 g/m². If the basis weight of the blood modifying agent is less than about 1 g/m², the blood modifying effect will tend to be insufficient, and if the basis weight of the blood modifying agent is increased, the stickiness during wearing will tend to be increased.

When the material to be coated with the blood modifying agent, such as, the top sheet, is a nonwoven fabric or porous film made of a synthetic resin, it is preferably coated with or mixed with a hydrophilic agent for hydrophilicizing treatment. If the original material is hydrophilic, since it is subsequently coated with a lipophilic modifying agent having an IOB of about 0.00-0.60 and high organicity, there will be created sparsely dispersed lipophilic regions and hydrophilic regions. This presumably allows consistent absorption performance to be exhibited for menstrual blood which consists of hydrophilic components (blood plasma, etc.) and lipophilic components (blood cells, etc.).

There are no particular restrictions on the method of coating the blood modifying agent, and coating may be accomplished with heating as necessary, using a non-contact coater, for example, a spiral coater, curtain coater, spray coater or dip coater, or a contact coater or the like. A non-contact coater is preferred from the viewpoint of uniformly dispersing the droplet or particulate modifying agent throughout, and from the viewpoint of not causing damage in the material. The blood modifying agent may be coated directly, if it is a liquid at room temperature, or it may be heated to lower the viscosity, and when it is a solid at room temperature, it may be heated to liquefaction and coated through a control seam hot melt adhesive (HMA) gun. By increasing the air pressure of the control seam HMA gun, it is possible to coat the blood modifying agent as fine particulates.

The blood modifying agent may be coated during production of the top sheet material, such as, the nonwoven fabric, or it may be coated in the manufacturing line for production of the absorbent article. From the viewpoint of minimizing equipment investment, the blood modifying agent is preferably coated in the manufacturing line for the absorbent article, and in order to prevent shedding of the blood modifying agent which may contaminate the line, the blood modifying agent is preferably coated during a step downstream from the manufacturing line, and specifically, immediately before encapsulation of the product in an individual package.

The blood modifying agent may also have an effect as a lubricant. When the top sheet is a nonwoven fabric, it is possible to reduce friction between fibers, thereby improving the flexibility of the nonwoven fabric as a whole. When the top sheet is a resin film, it is possible to reduce friction between the top sheet and the skin.

The absorbent article is preferably an absorbent article intended for absorption of blood, such as, a sanitary napkin, panty liner or the like.

With an absorbent article of this disclosure, there is no need for components such as, emollients and immobilizing agents, unlike absorbent articles containing a skin care composition, lotion composition or the like. In one or more embodiments, it is sufficient to apply to the top sheet the blood modifying agent alone.

EXAMPLES

Several examples will now be explained by examples, with the understanding that the disclosure is not meant to be limited to the examples.

Example 1

Evaluation of Rewetting Rate and Absorbent Body Migration Rate

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150-450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood modifying agents used for the experiment are listed below.

[($a_1$) Ester of a Chain Hydrocarbon Tetraol and at Least One Fatty Acid]

UNISTAR H-408BRS, Product of NOF Corp.
Tetrapentaerythritol 2-ethylhexanoate, weight-average molecular weight: approximately 640
UNISTAR H-2408BRS-22, Product of NOF Corp.
Mixture of tetrapentaerythritol 2-ethylhexanoate and di-neopentyl 2-ethylhexanoate glycol (58:42, mass ratio), weight-average molecular weight: approximately 520

[($a_2$) Ester of a Chain Hydrocarbon Triol and at Least One Fatty Acid]

Cetiol SB45DEO, Cognis Japan
Glycerin and fatty acid triester, with oleic acid or stearylic acid as the fatty acid.
SOY42, Product of NOF Corp.
Glycerin and fatty acid triester with $C_{14}$ fatty acid:$C_{16}$ fatty acid: $C_{18}$ fatty acid:$C_{20}$ fatty acid (including both saturated fatty acids and unsaturated fatty acids) at a mass ratio of about 0.2:11:88:0.8, weight-average molecular weight: 880
Tri-C2L Oil Fatty Acid Glyceride, Product of NOF Corp.
Glycerin and fatty acid triester with $C_8$ fatty acid:$C_{10}$ fatty acid:$C_{12}$ fatty acid at a mass ratio of about 37:7:56, weight-average molecular weight: approximately 570
Tri-CL Oil Fatty Acid Glyceride, Product of NOF Corp.
Glycerin and fatty acid triester with $C_8$ fatty acid:$C_{12}$ fatty acid at a mass ratio of about 44:56, weight-average molecular weight: approximately 570
PANACET 810s, Product of NOF Corp.
Glycerin and fatty acid triester with $C_8$ fatty acid:$C_{10}$ fatty acid at a mass ratio of about 85:15, weight-average molecular weight: approximately 480
PANACET 800, Product of NOF Corp.
Glycerin and fatty acid triester with octanoic acid ($C_8$) as the entire fatty acid portion, weight-average molecular weight: approximately 470
PANACET 800B, Product of NOF Corp.
Glycerin and fatty acid triester with 2-ethylhexanoic acid ($C_8$) as the entire fatty acid portion, weight-average molecular weight: approximately 470
NA36, Product of NOF Corp.
Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880
Tri-Coconut Fatty Acid Glyceride, Product of NOF Corp.
Glycerin and fatty acid triester with $C_8$ fatty acid: $C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670
Caprylic Acid Diglyceride, Product of NOF Corp.
Glycerin and fatty acid diester with octanoic acid as the fatty acid, weight-average molecular weight: approximately 340

[($a_3$) Ester of a Chain Hydrocarbon Diol and at Least One Fatty Acid]

COMPOL BL, Product of NOF Corp.
Dodecanoic acid ($C_{12}$) monoester of butylene glycol, weight-average molecular weight: approximately 270
COMPOL BS, Product of NOF Corp.
Octadecanoic acid ($C_{18}$) monoester of butylene glycol, weight-average molecular weight: approximately 350
UNISTAR H-208BRS, Product of NOF Corp.
Neopentylglycol di-2-ethylhexanoate, weight-average molecular weight: approximately 360.

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-Acetylcitrate, Product of Tokyo Kasei Kogyo Co., Ltd.
Weight-average molecular weight: approximately 400

[(c₃) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl Adipate, Product of Wako Pure Chemical Industries, Ltd.

Weight-average molecular weight: approximately 380

[(d₃) Ester of a Fatty Acid and an Aliphatic Monohydric Alcohol]

ELECTOL WE20, product of NOF Corp.

Ester of dodecanoic acid ($C_{12}$) and dodecyl alcohol ($C_{12}$), weight-average molecular weight: approximately 360

ELECTOL WE40, Product of NOF Corp.

Ester of tetradecanoic acid ($C_{14}$) and dodecyl alcohol ($C_{12}$), weight-average molecular weight: approximately 390

[(e₁) Polyoxy $C_3$-$C_6$ Alkylene Glycol]

UNIOL PB500, Product of NOF Corp.

Polybutylene glycol, weight-average molecular weight: approximately 500

UNIOL PB700, Product of NOF Corp.

Polyoxybutylenepolyoxypropylene glycol, weight-average molecular weight: approximately 700

[(f₁) Chain Alkane]

PARLEAM 6, Product of NOF Corp.

Branched hydrocarbon, produced by copolymerization of liquid isoparaffin, isobutene and n-butene followed by hydrogen addition, polymerization degree: approximately 5-10, weight-average molecular weight: approximately 330

[Other Components]

NA50, Product of NOF Corp.

Glycerin and fatty acid triester obtained by addition of hydrogen to NA36 for reduced proportion of double bonds from unsaturated fatty acid starting material, weight-average molecular weight: approximately 880

(Caprylic Acid/Capric Acid) Monoglyceride, Product of NOF Corp.

Glycerin and fatty acid monoester, with octanoic acid ($C_8$) and decanoic acid ($C_{10}$) at a mass ratio of about 85:15, weight-average molecular weight: approximately 220

Monomuls 90-L2 lauric acid monoglyceride, product of Cognis Japan

Isopropyl Citrate, Product of Tokyo Kasei Kogyo Co., Ltd.

Weight-average molecular weight: approximately 230

Diisostearyl Malate

Weight-average molecular weight: approximately 640

UNIOL PB1000R, Product of NOF Corp.

Polybutylene glycol, weight-average molecular weight: approximately 1,000

UNIOL D-400, Product of NOF Corp.

Polypropylene glycol, weight-average molecular weight: approximately 400

UNIOL D-1000, Product of NOF Corp.

Polypropylene glycol, weight-average molecular weight: approximately 1,000

UNIOL D-1200, Product of NOF Corp.

Polypropylene glycol, weight-average molecular weight: approximately 1,160

UNIOL D-3000, Product of NOF Corp.

Polypropylene glycol, weight-average molecular weight: approximately 3,000

UNIOL D-4000, Product of NOF Corp.

Polypropylene glycol, weight-average molecular weight: approximately 4,000

PEG1500, Product of NOF Corp.

Polyethylene glycol, weight-average molecular weight: approximately 1,500-1,600

WILBRITE Cp9, Product of NOF Corp.

Polybutylene glycol compound with OH groups at both ends esterified by hexadecanoic acid ($C_{16}$), weight-average molecular weight: approximately 1,150

UNILUBE MS-70K, Product of NOF Corp.

Stearyl ether of polypropylene glycol, approximately repeating units, weight-average molecular weight: approximately 1,140

NONION S-6, Product of NOF Corp.

Polyoxyethylene monostearate, approximately 7 repeating units, weight-average molecular weight: approximately 880

UNILUBE 5TP-300 KB

Polyoxyethylenepolyoxypropylene pentaerythritol ether, produced by addition of 5 mol of ethylene oxide and 65 mol of propylene oxide to 1 mol of pentaerythritol, weight-average molecular weight: 4,130

WILBRITE s753, Product of NOF Corp.

Polyoxyethylenepolyoxypropylene polyoxybutylene glycerin, weight-average molecular weight: approximately 960

UNIOL TG-330, Product of NOF Corp.

Glyceryl ether of polypropylene glycol, approximately 6 repeating units, weight-average molecular weight: approximately 330

UNIOL TG-1000, Product of NOF Corp.

Glyceryl ether of polypropylene glycol, approximately 16 repeating units, weight-average molecular weight: approximately 1,000

UNIOL TG-3000, Product of NOF Corp.

Glyceryl ether of polypropylene glycol, approximately 16 repeating units, weight-average molecular weight: approximately 3,000

UNIOL TG-4000, Product of NOF Corp.

Glyceryl ether of polypropylene glycol, approximately 16 repeating units, weight-average molecular weight: approximately 4,000

UNILUBE DGP-700, Product of NOF Corp.

Diglyceryl ether of polypropylene glycol, approximately 9 repeating units, weight-average molecular weight: approximately 700

UNIOX HC60, Product of NOF Corp.

Polyoxyethylene hydrogenated castor oil, weight-average molecular weight: approximately 3,570

Vaseline, Product of Cognis Japan

Petroleum-derived hydrocarbon, semi-solid

The IOBs, melting points, water solubilities and weight-average molecular weights of the samples are shown in Table 2.

The water solubility was measured by the method described above, and samples that dissolved 24 hours after addition of 20.0 g to 100 g of desalted water were evaluated as "20 g<", and samples of which 0.05 g dissolved in 100 g of desalted water but 1.00 g did not dissolve were evaluated as 0.05-1.00 g.

For the melting point, "<45" indicates a melting point of below 45° C.

The skin contact surface of the top sheet of the sanitary napkin was coated with the aforementioned blood modifying agent. Each blood modifying agent was used directly, when the blood modifying agent was liquid at room temperature, or when the blood modifying agent was solid at room temperature it was heated to its melting point of +20° C., and a control seam HMA gun was used for atomization of the blood modifying agent and coating onto the skin contact surface of the top sheet to a basis weight of about 5 g/m².

FIG. 1 is a view of Example 1, showing the region of the top sheet containing the blood modifying agent. As shown in FIG. 1, almost the entire surface of the top sheet 2 of the sanitary napkin 1 in Example 1 is the blood modifying agent-containing region 4 comprising the blood modifying agent. In FIG. 1, numeral 3 denotes a stamped section (groove or depression).

Figure 2:
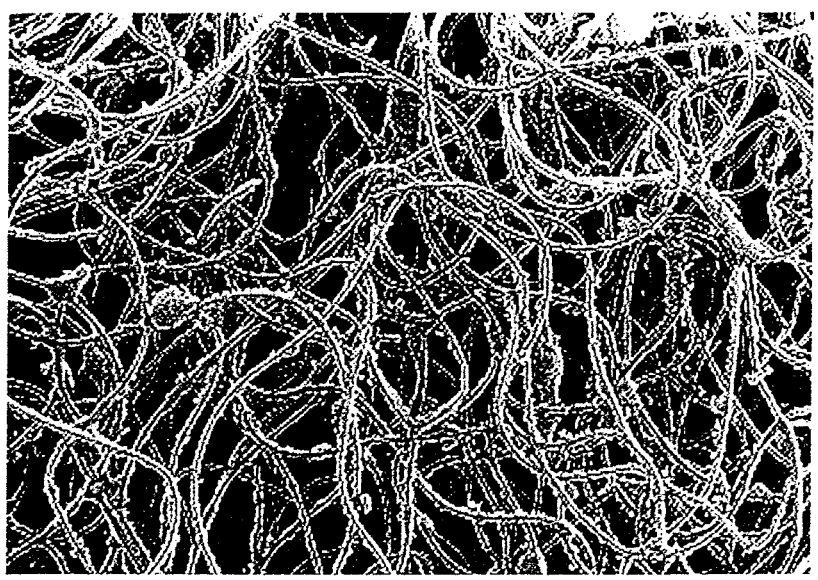
FIG. 2 is an electron micrograph of the skin contact surface of a top sheet in a sanitary napkin wherein the top sheet comprises tri-C2L oil fatty acid glycerides.

FIG. 2 is an electron micrograph of the skin contact surface of a top sheet in a sanitary napkin (No. 5) wherein the top sheet comprises tri-C2L oil fatty acid glycerides. As clearly seen in FIG. 2, the tri-C2L oil fatty acid glycerides are present on the fiber surfaces as fine particulates.

[Test Methods]

An acrylic board with an opened hole (200 mm×100 mm, 125 g, with a 40 mm×10 mm hole opened at the center) was placed on a top sheet comprising each blood modifying agent, and 3 g of horse EDTA blood at 37±1° C. (obtained by adding ethylenediaminetetraacetic acid (hereunder, "EDTA") to horse blood to prevent coagulation) was dropped through the hole using a pipette (once), and after 1 minute, 3 g of horse EDTA blood at 37±1° C. was again added dropwise through the acrylic board hole with a pipette (twice).

After the second dropping of blood, the acrylic board was immediately removed and 10 sheets of filter paper (Advantec Toyo Kaisha, Ltd, Qualitative Filter Paper No. 2, 50 mm×35 mm) were placed on the location where the blood had been dropped, and then a weight was placed thereover to a pressure of 30 g/cm². After 1 minute, the filter paper was removed and the "rewetting rate" was calculated by the following formula.

Rewetting rate (%)=100×(filter paper mass after test−initial filter paper mass)/6

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

The whiteness of the skin contact surface of the top sheet after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The results are summarized below in Table 2.

TABLE 2

| No. | Type | Blood modifying agent Product name | IOB | Melting point (° C.) | Water solubility (g) | Weight-average mol. wt. | Rewetting rate (%) | Absorber migration rate (sec) | Top sheet whiteness |
|---|---|---|---|---|---|---|---|---|---|
| 1 | (a₁) | H-408BRS | 0.13 | <−5 | <0.05 | 640 | 1.2 | 3 | VG |
| 2 | | H-2408BRS-22 | 0.18 | <−5 | <0.05 | 520 | 2.0 | 3 | VG |
| 3 | (a₂) | CETIOL SB45DEO | 0.16 | 44 | <0.05 | | 7.0 | 6 | VG |
| 4 | | SOY42 | 0.16 | 43 | <0.05 | 880 | 5.8 | 8 | VG |
| 5 | | Tri-C2L oil fatty acid glyceride | 0.27 | 37 | <0.05 | 570 | 0.3 | 3 | VG |
| 6 | | Tri-CL oil fatty acid glyceride | 0.28 | 38 | <0.05 | 570 | 1.7 | 3 | VG |
| 7 | | PANACET 810s | 0.32 | −5 | <0.05 | 480 | 2.8 | 3 | VG |
| 8 | | PANACET 800 | 0.33 | −5 | <0.05 | 470 | 0.3 | 3 | VG |
| 9 | | PANACET 800B | 0.33 | −5 | <0.05 | 470 | 2.0 | 3 | VG |
| 10 | | NA36 | 0.16 | 37 | <0.05 | 880 | 3.9 | 5 | VG |
| 11 | | Tri-coconut fatty acid glyceride | 0.28 | 30 | <0.05 | 670 | 4.3 | 5 | VG |
| 12 | | Caprylic acid diglyceride | 0.58 | <45 | <0.05 | 340 | 4.2 | 9 | G |
| 13 | (a₃) | COMPOL BL | 0.50 | 2 | <0.05 | 270 | 2.0 | 5 | G |
| 14 | | COMPOL BS | 0.36 | 37 | <0.05 | 350 | 7.9 | 9 | G |
| 15 | | H-208BRS | 0.24 | <−5 | <0.05 | 360 | 2.0 | 5 | VG |
| 16 | (c₂) | Tributyl O-acetylcitrate | 0.60 | <45 | <0.05 | 400 | 6.2 | 8 | VG |
| 17 | (c₃) | Dioctyl adipate | 0.27 | <45 | <0.05 | 380 | 1.7 | 6 | VG |
| 18 | (d₃) | ELECTOL WE20 | 0.13 | 29 | <0.05 | 360 | 1.8 | 5 | VG |
| 19 | | ELECTOL WE40 | 0.12 | 37 | <0.05 | 390 | 1.8 | 4 | VG |
| 20 | (e₁) | UNIOL PB500 | 0.44 | <45 | <0.05 | 500 | 4.5 | 4 | G |
| 21 | | UNIOL PB700 | 0.49 | −5 | <0.05 | 700 | 2.8 | 5 | G |
| 22 | (f₁) | PARLEAM 6 | 0.00 | −5 | <0.05 | 330 | 6.0 | 8 | VG |
| 23 | | NA50 | 0.18 | 52 | <0.05 | 880 | 15.5 | 60 | P |
| 24 | | (Caprylic acid/capric acid) monoglyceride | 1.15 | <45 | 20< | 220 | 4.0 | 4 | P |
| 25 | | 90-L2 lauric acid monoglyceride | 0.87 | 58 | 20< | | 6.2 | 7 | P |
| 26 | | Isopropyl citrate | 1.56 | <45 | 20< | 230 | 12.2 | 5 | G |
| 27 | | Diisostearyl malate | 0.28 | <45 | 20< | 640 | 5.5 | 8 | F |
| 28 | | UNIOL PB1000R | 0.40 | <45 | <0.05 | 1,000 | 4.0 | 4 | G |
| 29 | | UNIOL D-400 | 0.76 | <45 | 0.05< | 400 | 8.7 | 40 | P |
| 30 | | UNIOL D-1000 | 0.51 | <45 | <0.05 | 1,000 | 6.8 | 15 | F |
| 31 | | UNIOL D-1200 | 0.48 | <45 | <0.05 | 1,160 | 0.5 | 11 | F |
| 32 | | UNIOL D-3000 | 0.39 | <45 | <0.05 | 3,000 | 1.7 | 10 | F |
| 33 | | UNIOL D-4000 | 0.38 | <45 | <0.05 | 4,000 | 1.0 | 7 | G |
| 34 | | PEG1500 | 0.78 | 40 | 20< | 1,500–1,600 | 11.0 | 38 | P |
| 35 | | WILBRITE cp9 | 0.21 | 35 | <0.05 | 1,150 | 1.4 | 3 | G |
| 36 | | UNILUBE MS-70K | 0.30 | <−10 | <0.05 | 1,140 | 6.7 | 3 | G |
| 37 | | NONION S-6 | 0.44 | 37 | 0.05< | 880 | 8.4 | 7 | P |
| 38 | | UNILUBE 5TP-300KB | 0.39 | <45 | <0.05 | 4,130 | 2.0 | 6 | G |
| 39 | | WILBRITE s7- | 0.67 | −5 | 20< | 960 | 9.3 | 9 | F |
| 40 | | UNIOL TG-330 | 1.27 | <45 | 0.05< | 330 | — | — | — |

TABLE 2-continued

| No. | Blood modifying agent Type | Product name | IOB | Melting point (° C.) | Water solubility (g) | Weight-average mol. wt. | Rewetting rate (%) | Absorber migration rate (sec) | Top sheet whiteness |
|---|---|---|---|---|---|---|---|---|---|
| 41 | | UNIOL TG-1000 | 0.61 | <45 | <0.05 | 1,000 | 14.2 | 7 | G |
| 42 | | UNIOL TG-3000 | 0.42 | <45 | <0.05 | 3,000 | 0.8 | 6 | G |
| 43 | | UNIOL TG-4000 | 0.40 | <45 | <0.05 | 4,000 | 2.0 | 6 | G |
| 44 | | UNIOL DGP-700 | 0.91 | <0 | 0.05< | 700 | 8.0 | 10 | F |
| 45 | | UNIOX HC60 | 0.46 | 33 | 0.05-1.00 | 3,570 | 14.6 | 46 | P |
| 46 | | Vaseline | 0.00 | 55 | <0.05 | | 9.7 | 10 | F |
| 47 | | None | — | — | — | — | 22.7 | 60< | P |

In the absence of a blood modifying agent, the rewetting rate was 22.7% and the absorbent body migration rate was greater than 60 seconds, but the glycerin and fatty acid triesters all produced rewetting rates of no greater than 7.0% and absorbent body migration rates of no longer than 8 seconds, and therefore significantly improved the absorption performance. Of the glycerin and fatty acid triesters, however, no great improvement in absorption performance was seen with NA50 which had a melting point above 45° C.

Similarly, the absorption performance was also significantly improved with blood modifying agents having an IOB of about 0-0.60, a melting point of no higher than about 45° C., a water solubility of about 0.00-0.05 g in 100 g of water at 25° C., and a weight-average molecular weight of less than about 1,000.

Next, several volunteer subjects were asked to wear sanitary napkins Nos. 1-47, and the obtained responses indicated that with the sanitary napkins comprising blood modifying agents Nos. 1-22, the top sheets had no sticky feel and the top sheets were smooth, even after absorption of menstrual blood. The responses also indicated that the differences were notable with sanitary napkin Nos. 23, 29, 34, 45 and 47.

Also, with sanitary napkins Nos. 1-22, and particularly with sanitary napkins that comprised blood modifying agents Nos. 1-11, 15-19 and 22, the skin contact surfaces of the top sheets after absorption of menstrual blood had not been reddened by the blood and the unpleasantness was minimal.

Example 2

The rewetting rate was evaluated for blood from different animals. The following blood was used for the test.
[Animal Species]
(1) Human
(2) Horse
(3) Sheep
[Types of Blood]
Defibrinated blood: blood sampled and agitated together with glass beads in an Erlenmeyer flask for approximately 5 minutes.
EDTA blood: 65 mL of venous blood with addition of 0.5 mL of a 12% EDTA·0.2K isotonic sodium chloride solution.
[Fractionation]
Serum or blood plasma: Supernatant obtained after centrifugation of defibrinated blood or EDTA blood for 10 minutes at room temperature at about 1900 G.
Blood cells: Obtained by removing the serum from the blood, washing twice with phosphate buffered saline (PBS) and adding phosphate buffered saline to the removed serum portion.

An absorbent article was produced in the same manner as Example 1, except that the tri-C2L oil fatty acid glyceride was coated at a basis weight of about 5 g/m², and the rewetting rate of each of the aforementioned blood samples was evaluated. Measurement was performed 3 times for each blood sample, and the average value was recorded.

The results are shown in Table 3 below.

TABLE 3

| | | | Rewetting rate (%) | |
|---|---|---|---|---|
| No. | Animal species | Type of blood | With blood modifying agent | Without blood modifying agent |
| 1 | Human | Defibrinated blood | 1.6 | 5.0 |
| 2 | | Defibrinated serum | 0.2 | 2.6 |
| 3 | | Defibrinated blood cells | 0.2 | 1.8 |
| 4 | | EDTA blood | 2.6 | 10.4 |
| 5 | | EDTA plasma | 0.0 | 5.8 |
| 6 | | EDTA blood cells | 0.2 | 4.3 |
| 7 | Horse | Defibrinated blood | 0.0 | 8.6 |
| 8 | | Defibrinated serum | 0.2 | 4.2 |
| 9 | | Defibrinated blood cells | 0.2 | 1.0 |
| 10 | | EDTA blood | 6.0 | 15.7 |
| 11 | | EDTA plasma | 0.1 | 9.0 |
| 12 | | EDTA blood cells | 0.1 | 1.8 |
| 13 | Sheep | Defibrinated blood | 0.2 | 5.4 |
| 14 | | Defibrinated serum | 0.3 | 1.2 |
| 15 | | Defibrinated blood cells | 0.1 | 1.1 |
| 16 | | EDTA blood | 2.9 | 8.9 |
| 17 | | EDTA plasma | 0.0 | 4.9 |
| 18 | | EDTA blood cells | 0.2 | 1.6 |

The same trend was seen with human and sheep blood as with the horse EDTA blood, as obtained in Example 1. A similar trend was also observed with defibrinated blood and EDTA blood.

Example 3

Evaluation of Blood Retention

The blood retention was evaluated for a top sheet comprising a blood modifying agent and a top sheet comprising no blood modifying agent.
[Test Methods]
(1) A tri-C2L oil fatty acid glyceride was atomized on the skin contact surface of a top sheet formed from an air-through nonwoven fabric (composite fiber composed of polyester and polyethylene terephthalate, basis weight: 35 g/m²), using a control seam HMA gun, for coating to a basis weight of about 5 g/m². For comparison, there was also prepared a sheet without coating with the tri-C2L oil fatty acid glyceride. Next, both the tri-C2L oil fatty acid glyceride-coated top sheet and the non-coated top sheet were cut to a size of 0.2 g, and the mass (a) of the cell strainer+top sheet was precisely measured.

(2) After adding about 2 mL of horse EDTA blood from the skin contact surface side, it was allowed to stand for 1 minute.

(3) The cell strainer was set in a centrifuge tube, and subjected to spin-down to remove the excess horse EDTA blood.

(4) The mass (b) of the top sheet containing the cell strainer+horse EDTA blood was measured.

(5) The initial absorption (g) per 1 g of top sheet was calculated by the following formula.

Initial absorption=[mass (b)−mass (a)]/0.2

(6) The cell strainer was again set in the centrifuge tube and centrifuged at room temperature for 1 minute at approximately 1,200 G.

(7) The mass (c) of the top sheet containing the cell strainer+horse EDTA blood was measured.

(8) The post-test absorption (g) per 1 g of top sheet was calculated by the following formula.

Post-test absorption=[mass (c)−mass (a)]/0.2

(9) The blood retention (%) was calculated according to the following formula.

Blood retention (%)=100×post-test absorption/initial absorption

The measurement was conducted 3 times, and the average value was recorded.

The results are shown in Table 4 below.

TABLE 4

| | Blood retention (%) | |
|---|---|---|
| | With blood modifying agent | Without blood modifying agent |
| Horse EDTA blood | 3.3 | 9.2 |

The top sheets comprising blood modifying agents had low blood retentions, suggesting that blood rapidly migrated into the absorbent body after absorption.

Example 4

Viscosity of Blood Containing Blood Modifying Agent

The viscosity of the blood modifying agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood modifying agent was 50.4 mPa·s. Thus, the horse defibrinated blood containing 2 mass % PANACET 810s clearly had an approximately 90% lower viscosity than the blood containing no blood modifying agent.

It is known that blood contains components such as, blood cells and has thixotropy, and it has been found that the blood modifying agent of this disclosure can lower blood viscosity in the low viscosity range. Lowering the blood viscosity presumably allows absorbed menstrual blood to rapidly migrate from the top sheet to the absorbent body.

Example 5

Photomicrograph of Blood Modifying Agent-Containing Blood

Menstrual blood was sampled from healthy volunteers onto food wrap film, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood modifying agent is shown in FIG. 3(a), and a photomicrograph of menstrual blood containing PANACET 810s is shown in FIG. 3(b).

Figure 3:
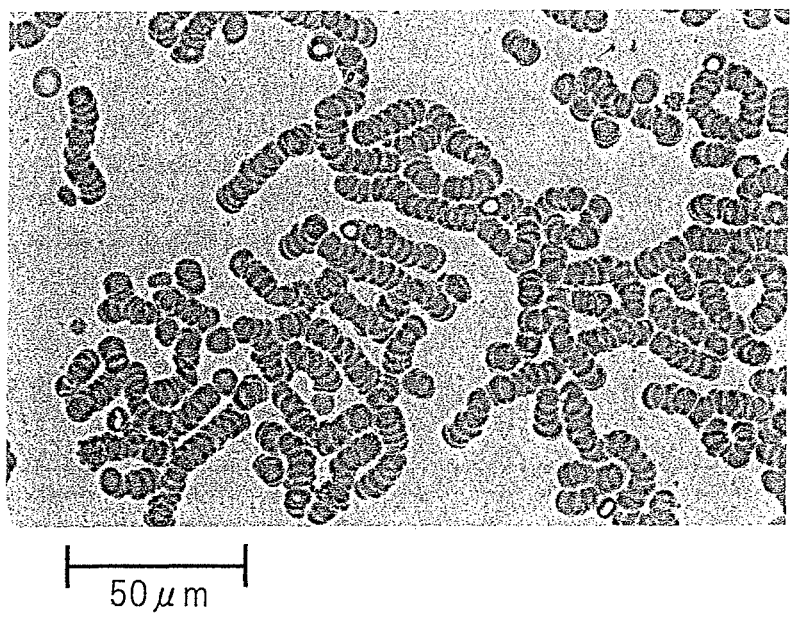
FIG. 3 is a pair of photomicrographs of menstrual blood containing and not containing a blood modifying agent.
Figure 3:
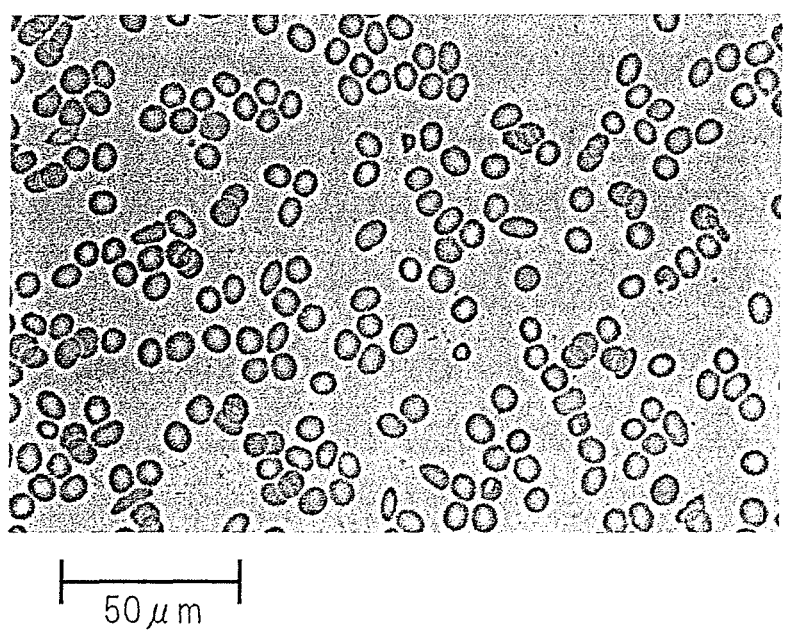

As shown in FIG. 3(a), it is seen that the erythrocytes formed aggregates such as, rouleaux in the menstrual blood containing no blood modifying agent, while as shown in FIG. 3(b), the erythrocytes were stably dispersed in the menstrual blood containing PANACET 810s. This suggests that the blood modifying agent functions to stabilize erythrocytes in blood.

Example 6

Surface Tension of Blood Containing Blood Modifying Agent

The surface tension of blood containing a blood modifying agent was measured by the pendant drop method, using a Drop Master500 contact angle meter by Kyowa Interface Science Co., Ltd. The surface tension was measured after adding a prescribed amount of blood modifying agent to sheep defibrinated blood, and thoroughly shaking.

Figure 4:
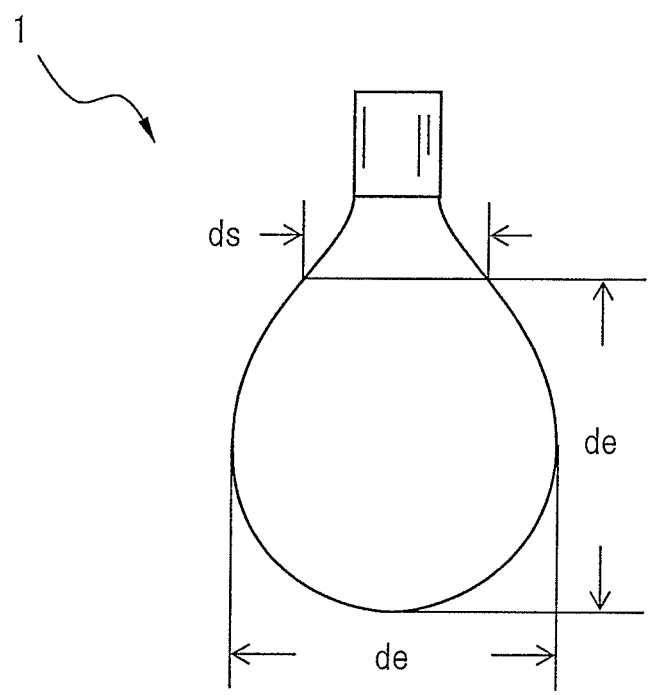
FIG. 4 is a diagram illustrating a method of measuring surface tension.

The measurement was accomplished automatically with a device, and the density γ was determined by the following formula (see FIG. 4).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 5, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 5 below.

TABLE 5

| | Blood modifying agent | | | |
|---|---|---|---|---|
| No. | Type | Amount (mass %) | Measuring temperature (° C.) | Surface tension (mN/m) |
| 1 | — | — | 35 | 62.1 |
| 2 | PANACET | 0.01 | 35 | 61.5 |

TABLE 5-continued

| | Blood modifying agent | | | |
|---|---|---|---|---|
| No. | Type | Amount (mass %) | Measuring temperature (° C.) | Surface tension (mN/m) |
| 3 | 810s | 0.05 | 35 | 58.2 |
| 4 | | 0.10 | 35 | 51.2 |
| 5 | ELECTOL WE20 | 0.10 | 35 | 58.8 |
| 6 | PARLEAM 6 | 0.10 | 35 | 57.5 |
| 7 | — | — | 50 | 56.3 |
| 8 | WILBRITE cp9 | 0.10 | 50 | 49.1 |

Table 5 shows that the blood modifying agent can lower the surface tension of blood despite its very low solubility in water, as seen by a water solubility of 0.00-0.05 g in 100 g of water at 25° C.

Lowering the surface tension of blood presumably allows absorbed blood to rapidly migrate from the top sheet to the absorbent body, without being retained between the top sheet fibers.

The present disclosure relates to the following J1 to J8.

[J1]

An absorbent article comprising a liquid-permeable top sheet, a liquid-impermeable back sheet and an absorbent body between the liquid-permeable top sheet and liquid-impermeable back sheet,
wherein the liquid-permeable top sheet comprises a blood modifying agent with an IOB of 0.00-0.60, a melting point of no higher than 45° C., a water solubility of 0.00-0.05 g in 100 g of water at 25° C., and a weight-average molecular weight of less than 1,000.

[J2]

The absorbent article according to J1, wherein the blood modifying agent is selected from the group consisting of following items (i)-(iii), and any combination thereof:
 (i) a hydrocarbon;
 (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
 (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting a hydrogen of the hydrocarbon moiety;
with the proviso that when 2 or more oxy groups are inserted in the compound of (ii) or (iii), the oxy groups are not adjacent.

[J3]

The absorbent article according to J1 or J2, wherein the blood modifying agent is selected from the group consisting of following items (i')-(iii'), and any combination thereof:
 (i') a hydrocarbon;
 (ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
 (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;
with the proviso that when 2 or more same or different bonds are inserted in the compound of (ii') or (iii'), the bonds are not adjacent.

[J4]

The absorbent article according to any one of J1 to J3, wherein the blood modifying agent is selected from the group consisting of following items (A)-(F), and any combination thereof:
 (A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;
 (B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;
 (C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;
 (D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety;
 (E) a polyoxy $C_3$-$C_6$ alkylene glycol, or alkyl ester or alkyl ether thereof; and
 (F) a chain hydrocarbon.

[J5]

The absorbent article according to any one of J1 to J4, wherein the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycol and at least one fatty acid, ($e_3$) an ether of a polyoxy $C_3$-$C_6$ alkylene glycol and at least one aliphatic monohydric alcohol, and ($f_1$) a chain alkane, and any combination thereof.

[J6]

The absorbent article according to any one of J1 to J5, wherein the blood modifying agent has the vapor pressure of 0.00-0.01 Pa at 1 atmosphere, 40° C.

[J7]

The absorbent article according to any one of J1 to J6, wherein the blood modifying agent has a weight-average molecular weight of no greater than 900.

[J8]

The absorbent article according to any one of J1 to J7, wherein the liquid-permeable top sheet is a nonwoven fabric or woven fabric, and the blood modifying agent is attached to the surfaces of the fibers of the nonwoven fabric or woven fabric.

[J9]

The absorbent article according to any one of J1 to J8, which is a sanitary napkin or panty liner.

This application claims the benefits of Japanese Application Nos. 2011-079446 and 2011-192144 the entire disclosures of which are incorporated by reference herein.

REFERENCES SIGNS LIST

1 Sanitary napkin
2 Top sheet
3 Stamped section
4 Blood modifying agent-containing region

The invention claimed is:

1. An absorbent article comprising:
a liquid-permeable top sheet,
a liquid-impermeable back sheet,
an absorbent body between the liquid-permeable top sheet and liquid-impermeable back sheet;
a substantially uniform coating on the liquid-permeable top sheet, wherein the coating is present at least at a center region of the article that is configured to be positioned near a vaginal opening in use, wherein the coating consists of a blood modifying agent having an Inorganic Organic Balance (JOB) of 0.00-0.60, a melting point of no higher than 45° C., a water solubility of 0.00-0.05 g in 100 g of water at 25° C., a chemical composition consisting of carbon and hydrogen atoms or carbon, hydrogen and oxygen atoms, and a weight-average molecular weight of less than 1,000, wherein the coating is configured to migrate into the absorbent body with menstrual blood, and the coating is free of each of polypropylene glycol copolymer, an ester of a polyoxy $C_3$-$C_6$ alkylene glycol and at least one fatty acid, and an ether of a polyoxy $C_3$-$C_6$ alkylene glycol and at least one aliphatic monohydric alcohol;
a second sheet between the top sheet and the absorbent body; and
a second coating on the second sheet, wherein the second coating comprises the blood modifying agent.

2. The absorbent article according to claim 1, wherein the blood modifying agent is selected from the group consisting of following items (i)-(iii), and any combination thereof:
(i) a hydrocarbon;
(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
(iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting a hydrogen of the hydrocarbon moiety;
with the proviso that when 2 or more oxy groups are inserted in the compound of (ii) or (iii), the oxy groups are not adjacent.

3. The absorbent article according to claim 1, wherein the blood modifying agent is selected from the group consisting of following items (i')-(iii'), and any combination thereof:
(i') a hydrocarbon;
(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
(iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting a hydrogen on the hydrocarbon moiety;
with the proviso that when 2 or more same or different bonds are inserted in the compound of (ii') or (iii'), the bonds are not adjacent.

4. The absorbent article according to claim 1, wherein the blood modifying agent is selected from the group consisting of following items (A)-(E), and any combination thereof:
(A) an ester of (A1) a compound having a chain hydrocarbon moiety and 2-4 hydroxyl groups substituting hydrogens on the chain hydrocarbon moiety, and (A2) a compound having a chain hydrocarbon moiety and 1 carboxyl group substituting a hydrogen on the chain hydrocarbon moiety;
(B) an ether of (B1) a compound having a chain hydrocarbon moiety and 2-4 hydroxyl groups substituting hydrogens on the chain hydrocarbon moiety and (B2) a compound having a chain hydrocarbon moiety and 1 hydroxyl group substituting a hydrogen on the chain hydrocarbon moiety;
(C) an ester of (C1) a carboxylic acid, hydroxy acid, alkoxy acid or oxoacid comprising a chain hydrocarbon moiety and 2-4 carboxyl groups substituting hydrogens on the chain hydrocarbon moiety and (C2) a compound having a chain hydrocarbon moiety and 1 hydroxyl group substituting a hydrogen on the chain hydrocarbon moiety;
(D) a compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety; and
(E) a chain hydrocarbon.

5. The absorbent article according to claim 1, wherein the blood modifying agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, and ($e_1$) a chain alkane, and any combination thereof.

6. The absorbent article according to claim 1, wherein the blood modifying agent has a vapor pressure of 0.00-0.01 Pa at 1 atmosphere, 40° C.

7. The absorbent article according to claim 1, wherein the blood modifying agent has a weight-average molecular weight of no greater than 900.

8. The absorbent article according to claim 1, wherein
the liquid-permeable top sheet is a nonwoven fabric or woven fabric, and
the blood modifying agent is attached to the surfaces of the fibers of the nonwoven fabric or woven fabric.

9. The absorbent article according to claim 1, which is a sanitary napkin or panty liner.

10. The absorbent article according to claim 1, wherein the blood modifying agent is configured to lower a blood viscosity and a surface tension of the liquid-permeable top sheet to
cause clogging of menstrual blood between top sheet fibers to be reduced and
cause menstrual blood to migrate from the top sheet to the absorbent body.

* * * * *